United States Patent
Tselepis et al.

(10) Patent No.: US 10,138,261 B2
(45) Date of Patent: Nov. 27, 2018

(54) FERROCENYL COMPOUNDS

(71) Applicant: The University of Birmingham, Birmingham (GB)

(72) Inventors: Chris Tselepis, Birmingham (GB); James Tucker, Birmingham (GB); Huy Van Nguyen, Birmingham (GB); Nikolas John Hodges, Birmingham (GB); Youcef Mehellou, Birmingham (GB)

(73) Assignee: THE UNIVERSITY OF BIRMINGHAM EDGBASTON, Birmingham (GB)

( * ) Notice: Subject to any disclaimer, the term of this patent is extended or adjusted under 35 U.S.C. 154(b) by 35 days.

(21) Appl. No.: 15/105,899

(22) PCT Filed: Dec. 19, 2014

(86) PCT No.: PCT/GB2014/053794
§ 371 (c)(1),
(2) Date: Jun. 17, 2016

(87) PCT Pub. No.: WO2015/092432
PCT Pub. Date: Jun. 25, 2015

(65) Prior Publication Data
US 2016/0318964 A1 Nov. 3, 2016

(30) Foreign Application Priority Data
Dec. 20, 2013 (GB) .................................. 1322752.5

(51) Int. Cl.
*C07F 17/02* (2006.01)
(52) U.S. Cl.
CPC .................................... *C07F 17/02* (2013.01)
(58) Field of Classification Search
None
See application file for complete search history.

(56) References Cited

PUBLICATIONS

Patin et al., Bulletin de la Societe Chimique de France, 1973, Issue 9-10 Pt. 2, pp. 2756-2759; Abstract only.*
McGuigan, C. et al., J. Med. Chem. 1993, 36, 1048-1052.
McGuigan, C. et al., J. Med. Chem. 1996, 39, 1748-1753.
McGuigan, C. et al., Antiviral Res. 1997, 35, 195-204.
Kowalski, K. et al., J. Organomet. Chem. 2012, 700, 58-68.
Simenel, A. A. et al., Appl. Organomet. Chem. 2009, 23, 219-224.
Kowalski, K. et al., Organometallics 2013, 32, 5766-5773.
Shago, F. R. et al., Anticancer Res. 2007, 27, 3431-3434.
James, P. et al., Org. Lett. 2006, 8, 2763-2766.
Marquarding, D. et al., J. Am. Chem. Soc. 1970, 92, 5389-5393.
Cruickshank, A. K. et al., Tetrahedron Lett. 1984, 25, 681-684.
Schaarschmidt, D. et al., Organometallics 2010, 29, 4196-4198.
Onishi, M. et al., J. Organomet. Chem. 1984, 262, C11-C13.
Barry, P. K. et al., Inorganica. Chimica. Acta. 2009, 362, 2068-2070.
UK Search Report dated Aug. 13, 2014, Application No. GB1322752.5.
Biot, C., et al., "Synthetic ferrocenic mefloquine and quinine analogues as potential antimalarial agents", European Journal of Medicinal Chemistry, vol. 35, No. 7-8, 2000, pp. 707-714.
Chiba, J., et al., "Electrochemical direct detection of DNA deamination catalyzed by APOBEC3G", Chemical Communications, vol. 48, 2012, pp. 12115-12117.
Miao, B., et al., "Directed ortho Metalation of Ferrocenes. Ring-substituted fulvenes by Nesmeyanov ferrocenylcarbenium ion fragmentation", Tetrahedron Letters, vol. 40, No. 13, 1999, pp. 2449-2452.
Nguyen, H.V., et al., "A ferrocene nucleic acid oligomer as an organometallic structural mimic of DNA", Chemical Communications, vol. 48, 2012, pp. 12165-12167.
Roque, K., et al., "New chiral ferrocenyl-pyridinium salts for non-linear optics", Journal of Organometallic Chemistry, vol. 637-639, 2001, pp. 531-537.
Steurer, M., et al., "Bromide-mediated ortho-deprotonation in the synthesis of chiral, nonracemic ferrocene derivatives", Organometallics, vol. 26, No. 15, 2007, pp. 3850-3859.

(Continued)

*Primary Examiner* — Savitha M Rao
*Assistant Examiner* — Gregg Polansky
(74) *Attorney, Agent, or Firm* — Gates & Cooper LLP

(57) ABSTRACT

A ferrocenyl compound having the general formula (I): (I) Het is a substituted or unsubstituted heterocyclic moiety. L1, L2 and L3 are each a linker independently selected from alkylene, alkyleneoxy, alkyleneoxyalkylene, alkylenecarbonyl, alkyleneoxycarbonyl, alkyleneamido, alkyleneoxyamido, alkenylene, alkenyleneoxy, alkenylenecarbonyl, alkenyleneamido, alkynylene, alkynyleneoxy, alkynylenecarbonyl and alkynyleneamido, all of which may be straight chain or branched, substituted or unsubstituted. $R^1$ and $R^2$ are each independently selected from H, substituted or unsubstituted alkyl carbonyl, substituted or unsubstituted aryl carbonyl, substituted or unsubstituted phosphate, substituted or unsubstituted phosphonate and substituted or unsubstituted phosphoramidate. M and n are each 0 or 1 and m+n≠0.1.

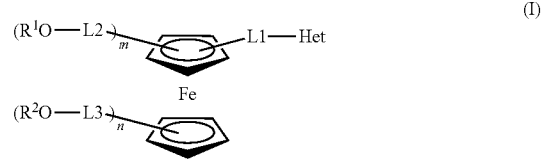

13 Claims, 3 Drawing Sheets

(56) References Cited

PUBLICATIONS

Figure 1:
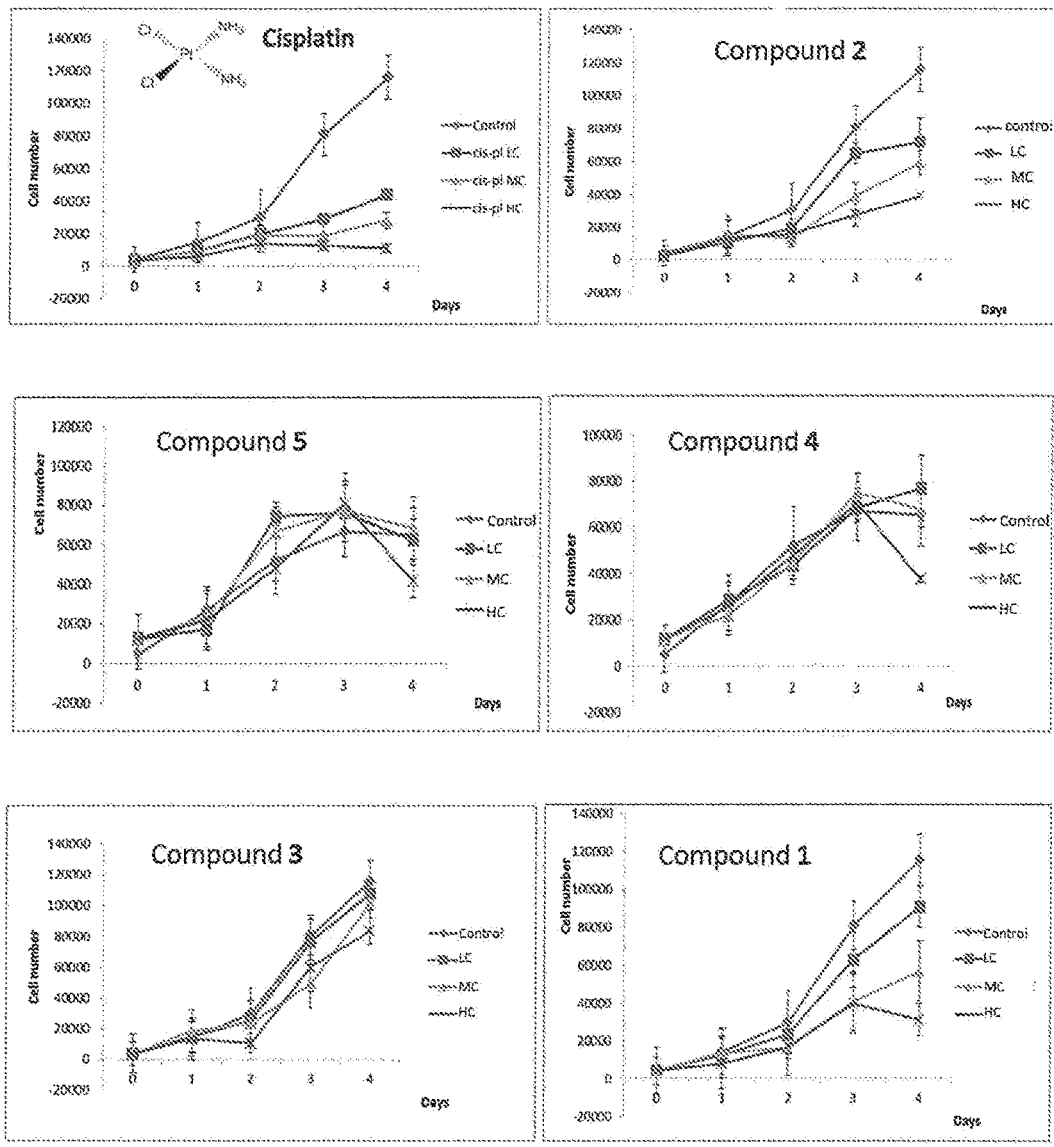

Watanabe, M., et al., "Chiral auxiliaries for Asymmetric Synthesis: Enantioselective Addition of Dialkylzincs to Aldehydes Catalyzed by Chiral 1,2-Disubstituted Ferrocenyl Amino Alcohols", Journal of Organic Chemistry, vol. 56, No. 6, 1991, pp. 2218-2224.

Widhalm, M., et al., "Chiral ferrocene derivatives containing a 2,2'-bridged binaphthyl moiety", Tetrahendron: Asymmetry, vol. 10, No. 22, 1999, pp. 4369-4391.

* cited by examiner

FERROCENYL COMPOUNDS

The invention relates to ferrocenyl compounds, in particular to ferrocenyl compounds comprising a heterocyclic moiety and more particularly to ferrocenyl compounds comprising a nucleobase moiety. The invention also relates to uses of the ferrocenyl compounds.

Nucleoside analogues have long been established as an effective class of compound that exhibit antiviral or anticancer activity. Their most common structural features are a nucleobase moiety and a hydroxylmethyl group, which together allow them to act as substrates that adversely affect processes associated with nucleic acid synthesis. These two components are typically connected by an organic linker group that is a modification or a replacement of the sugar ring, which can either be cyclic or acyclic. In the antiviral AZT, for example, the 3'-hydroxyl group of the sugar ring is replaced by the azido group.

The mechanism of action of nucleoside analogues is believed to proceed via phosphorylation of the primary alcohol by enzymatic processes into a triphosphate. This triphosphate can mistakenly be taken up by DNA polymerase to build new DNA sequences and causes chain termination. The first phosphorylation is often the rate determining step. It has been has reported that the Protide approach, which uses masked phosphate groups as prodrugs, by-passes this rate determining step and therefore significantly increases the availability of the active compounds to the DNA polymerase to terminate DNA synthesis (McGuigan, C. et al., *J. Med. Chem.* 1993, 36, 1048; McGuigan, C. et al., *J. Med. Chem.* 1996, 39, 1748; McGuigan, C. et al., *Antiviral Res.* 1997, 35, 195).

Due to their structural similarities to natural nucleosides, which can lead to resistance and side effects, there is a continuing need for a diverse range of nucleoside analogues with different structural features. Ferrocene has attracted ongoing and active interest in recent years within the field of medicinal and bioorganometallic chemistry, due to its unique structure, low toxicity, and redox properties. For example, the ferrocene analogue of chloroquine, ferroquine, is more active than chloroquine itself, and is also active against chloroquine resistant strains. Other examples of ferrocene containing compounds, such as ferrocifens and ferrocenylpenicillins, have shown antitumor, antibacterial and antifungal properties.

There are also some examples of ferrocene-conjugated nucleobases (Kowalski, K. et al., *J. Organomet. Chem.* 2012, 700, 58; Simenela, A. A. et al., *Appl. Organomet. Chem.* 2009, 23, 219; Kowalski, K. et al., *Organometallics* 2013, 32, 5766) and hydroxylalkyl ferrocenes (Shago, F. R. et al., *Anticancer Res.* 2007, 27, 3431) that exhibit antitumour activity. These ferrocene derivatives contain either a nucleobase moiety or a hydroxylalkyl substituent but not both. In the examples of ferrocene-containing nucleobases, the nucleobase is attached to one of the cyclopentadiene rings via a linker group which may be an alkylene chain, an alkenylene chain or an alkylenecarbonyl chain.

A ferrocene derivative containing both a nucleobase moiety and a hydroxylalkyl group has previously been reported but it did not show apoptosis-inducing activity against tumour cells (James, P. et al., *Org. Lett.* 2006, 8, 2763). In this reported derivative, one of the cyclopentadiene rings had been modified to form a tetrahydropentalene ring system, and the nucleobase moiety and hydroxylalkyl groups were substituents on the tetrahydropentalene ring system.

In light of the continuing need for a diverse range of ferrocenyl compounds with different structural features, it is an object of the present invention to provide novel ferrocenyl compounds which exhibit anticancer and/or antiviral activity.

According to a first aspect of the present invention there is provided a ferrocenyl compound having the general formula (I)

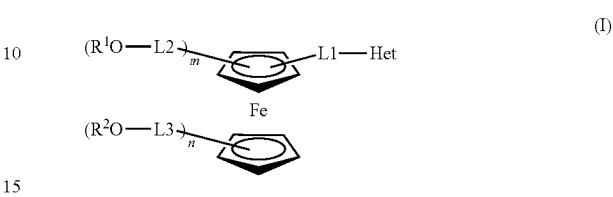

wherein
Het is a substituted or unsubstituted heterocyclic moiety;
L1, L2 and L3 are each a linker independently selected from alkylene, alkyleneoxy, alkyleneoxyalkylene, alkylenecarbonyl, alkyleneoxycarbonyl, alkyleneamido, alkyleneoxyamido, alkenylene, alkenyleneoxy, alkenylenecarbonyl, alkenyleneamido, alkynylene, alkynyleneoxy, alkynylenecarbonyl and alkynyleneamido, all of which may be straight chain or branched, substituted or unsubstituted;
$R^1$ and $R^2$ are each independently selected from H, substituted or unsubstituted alkylcarbonyl, substituted or unsubstituted arylcarbonyl, substituted or unsubstituted phosphate, substituted or unsubstituted phosphonate and substituted or unsubstituted phosphoramidate;
m and n are each 0 or 1; and
m+n≠0.

It will be appreciated by the skilled person that normal valency rules apply and that where substitution gives rise to chirality, both S- and R-isomers are independently claimed.

In some embodiments the linkers (and ferrocenyl moiety, Fc) may each be independently represented by one of the formulae (II), (III) or (IV):

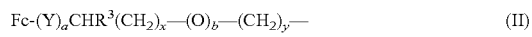

wherein
Y is —(CO)—, —O— or (CO)NR$^4$
$R^3$ is H, alkyl or halo
$R^4$ is H or alkyl
a and b are each 0 or 1
x+y≤5
z≤4

In some embodiments $R^3$ is H.
In some embodiments $R^4$ is H.
In some embodiments a is 0.
In some embodiments b is 0.
In some embodiments x+y≤3
In some embodiments z≤2
In some embodiments the linker contains no more than 6, no more than 5 or no more than 4 C atoms.
In some embodiments all of L1, L2 and L3 are the same.
In some embodiments two of L1, L2 and L3 are the same.
In some embodiments L1, L2 and L3 are all different to each other.

In some embodiments, the substituted or unsubstituted heterocyclic moiety (Het) is a nitrogen containing heterocycle. In some embodiments, Het is aromatic. In some embodiments, Het is a monocyclic, bicyclic or tricyclic heterocycle.

In some embodiments, the heterocyclic moiety (Het) is a pyrimidine nucleobase. In some embodiments, Het is selected from uracil, cytosine or thymine. In some embodiments, Het is thymine. In some embodiments, Het is a substituted pyrimidine nucleobase. The substituted pyrimidine base may be a substituted uracil or cytosine base. The uracil or cytosine base may be substituted at the 3- or 5-position.

In some embodiments, the heterocyclic moiety (Het) is a purine nucleobase. In some embodiments, Het is selected from adenine or guanine. In some embodiments, Het is adenine. In some embodiments, Het is a substituted purine nucleobase. The substituted purine base may be a substituted adenine or guanine base. In some embodiments, the adenine or guanine base may be substituted at the 7-position. In some embodiments, the adenine base may be substituted at the 2-position. In some embodiments, the guanine base may be substituted at the 1-position.

Suitable substituents for the purine and pyrimidine bases are known in the art. Non-limiting examples of suitable substituents are halides (for example fluoride, chloride, bromide), straight and branched chain alkyls (for example methyl, ethyl, trifluoromethyl), unsubstituted and substituted amines (for example amino, aminocyclopropane), and hydroxylalkyls.

In some embodiments, the heterocyclic moiety (Het) may be a substituted or unsubstituted triazole. In some embodiments, the triazole is substituted at the 3-position. In some embodiments the triazole is

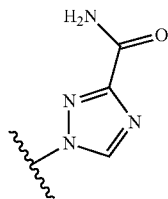 [SMILES: *n1cnc(C(N)=O)n1]

In some embodiments, the heterocyclic moiety may be a substituted or unsubstituted furopyrimidine moiety. In some embodiments, the furopyrimidine moiety is

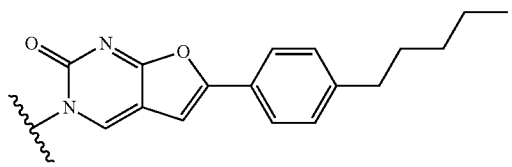 [SMILES: *n1cc2cc(-c3ccc(CCCCC)cc3)oc2nc1=O]

In some embodiments, the heterocyclic moiety may be a substituted pentaazaacenaphthylene. In some embodiments, the pentaazaacenaphthylene is

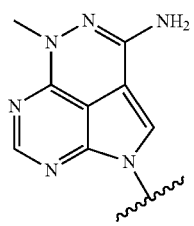 [SMILES: *n1cc2c3c(ncnc31)N(C)N=C2N]

It is to be understood that the ferrocenyl compounds of the present invention comprise a heterocyclic moiety L1-Het and at least one L2-$OR^1$ and/or L3-$OR^2$ group.

In some embodiments, m+n=1. The ferrocene moiety is therefore di-substituted. In some embodiments, m is 1 and n is 0, the L2-$OR^1$ group and the heterocyclic moiety L1-Het being substituents on the same cyclopentadiene ring.

In some embodiments, n is 1 and m is 0, the L3-$OR^2$ group and the heterocyclic moiety L1-Het being substituents on different cyclopentadiene rings.

In some embodiments, m and n are each 1 and so the L2-$OR^1$ and L3-$OR^2$ groups are both present. The ferrocene moiety is therefore tri-substituted. In such embodiments, it is to be understood that the L2-$OR^1$ and L3-$OR^2$ groups are present on different cyclopentadiene rings.

In some embodiments, in which m is 1, the L2-$OR^1$ group and the L1-Het heterocyclic moiety are present in a 1,2-disubstituted arrangement on the cyclopentadiene ring.

In embodiments in which m is 1, the ferrocenyl compound will have planar chirality. In some embodiments, the ferrocenyl compound may have a planar chirality of ($R_p$) configuration. In some embodiments, the ferrocenyl compound may have a planar chirality of ($S_p$) configuration. It is to be understood that the 'p' subscript refers to planar chirality.

Without wishing to be bound by theory, in embodiments in which either (or both) $R^1$ or $R^2$ is H, it is believed that the (or at least one) hydroxyl group is phosphorylated by a phosphorylation enzyme in the target cell to a triphosphate which is subsequently incorporated into DNA.

In some embodiments, the functionality of the hydroxyl group(s) may be masked, for example when either (or both) $R^1$ or $R^2$ is substituted or unsubstituted alkylcarbonyl or substituted or unsubstituted arylcarbonyl (i.e. $R^1$ and/or $R^2$ is C(O)$R^5$). In embodiments where $R^5$ is alkyl, the alkyl group may be linear or branched. Masking the hydroxyl group(s) in such a way, may for example, improve the transport of the ferrocenyl compound across the cell membrane. It is believed that once such compounds are inside the cell, the masking group is chemically or enzymatically removed to release the hydroxyl group(s) for subsequent phosphorylation.

In some embodiments, either (or both) $R^1$ or $R^2$ may be substituted or unsubstituted phosphate or phosphonate. It is known, for example, that unsubstituted phosphates (i.e. $R^1$ and/or $R^2$ is P(O)(OH)$_2$) and phosphonates (i.e. $R^1$ and/or $R^2$ is CH$_2$P(O)(OH)$_2$) may have poor cell permeability due to the charges associated with the phosphate or phosphonate groups. Therefore, the present invention includes within its scope, substituted phosphates (i.e. $R^1$ and/or $R^2$ is P(O)($OR^6$)($OR^7$)) and substituted phosphonates (i.e. $R^1$ and/or $R^2$ is CH$_2$P(O)($OR^8$)($OR^9$)). Non limiting examples of such substituted phosphates and phosphonates may include mono- and di-phosphate esters or mono- and di-phosphonate esters, which may be liner, branched or further substituted.

It is to be understood that such substituents 'mask' or 'protect' the phosphate or phosphonate group to improve the transport of the ferrocenyl compounds across the cell membrane. Once in the cell, the masking or protecting group is chemically and/or enzymatically degraded to release the monophosphate or monophosphonate, which undergoes further enzymatic phosphorylation. A further advantage of using such $R^1$ and/or $R^2$ groups is that the first rate limiting phosphorylation step of the hydroxyl group can be avoided.

In some embodiments, either (or both) $R^1$ or $R^2$ may be substituted or unsubstituted phosphoramidate (i.e. $R^1$ and/or $R^2$ is P(O)(OH)(NH$_2$) or P(O)($OR^{10}$)($NR^{11}R^{12}$)). In some embodiments, the derivative thereof may be an aryloxyphosphoramidate. In some embodiments, either (or both) $R^1$ or $R^2$ may be selected from

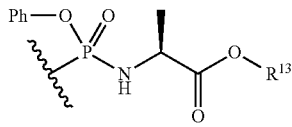

wherein, $R^{13}$ may be $C_1$ to $C_6$ alkyl, which may be linear or branched, substituted or unsubstituted. In some embodiments, $R^{13}$ may be methyl, isopropyl or substituted or unsubstituted benzyl.

Without wishing to be bound by theory, it is believed that substituted phosphoramidates act as masked phosphate groups and improve the transport of the compound across the cell membrane. Once inside the cell, the substituted phosphoramidate is cleaved, typically enzymatically, to release the monophosphate. This approach therefore circumvents the need for the first enzymatic phosphorylation which can sometimes be problematic. As discussed above, the monophosphate can then undergo further enzymatic phosphorylation to give the triphosphate for incorporation into DNA. Further advantages of such substituted phosphoramidates may include increased activity, increased stability and relative ease of preparation.

In some embodiments, the ferrocenyl compounds may be in the form of pharmaceutically acceptable salts thereof. Pharmaceutically acceptable salts may be stable, non-toxic and therapeutically active salts which can form with the ferrocenyl compounds of the present invention. Non-limiting examples of such salts include acetate, citrate, tosylate, tartrate, sulphate or hydrochloride salts.

According to a second aspect of the invention, there is provided a pharmaceutical composition comprising the ferrocenyl compounds or pharmaceutically acceptable salts thereof, of the first aspect of the invention.

The pharmaceutical compositions of the present invention may comprise a therapeutically-effective amount of the ferrocenyl compounds of general formula (I) or pharmaceutically acceptable salts thereof, as an active ingredient.

The pharmaceutical compositions of the present invention may further comprise one or more additional pharmaceutically acceptable ingredients such as carriers, excipients, bulking agents, diluents, buffers, flavouring agents, binders, surface active agents, thickeners, lubricants and preservatives.

The pharmaceutical compositions of the present invention may be delivered by enteral administration, for example orally; by parenteral administration, for example by intravenous, intramuscular or subcutaneous injection; or by topical administration, for example by inhalation or dermally.

For oral administration, the pharmaceutical composition may be in the form of discrete units such as capsules, tablets or lozenges; in the form of granules or a powder; or in liquid form such as an emulsion, suspension, solution or syrup.

For administration via injection, the pharmaceutical composition may be in the form of a liquid such as a solution, suspension or emulsion.

For topical administration, the pharmaceutical composition may be in the form of a powder, granules, a suspension, a solution, an emulsion, a cream or a paste.

According to a third aspect of the invention, there is provided the ferrocenyl compounds or pharmaceutically acceptable salts thereof, of the first aspect of the invention, or a pharmaceutical composition of the second aspect of the invention, for use as a medicament.

The subject of treatment may be a mammal and preferably a human.

According to a fourth aspect of the invention, there is provided the ferrocenyl compounds or pharmaceutically acceptable salts thereof, of the first aspect of the invention, or a pharmaceutical composition of the second aspect of the invention, for use in the treatment of cancer.

Such cancers may include blood, brain, mouth, neck, breast, lung, stomach, liver, pancreatic, bladder, ovarian, testicular, cervical, oesophageal or colorectal cancer or leukemia.

Treatment may comprise administering a therapeutically effective amount of the ferrocenyl compounds or pharmaceutically acceptable salts thereof, of the first aspect of the invention, or a pharmaceutical composition of the second aspect of the invention, to a subject in need thereof.

It would be within the capability of the skilled person to work out an appropriate dosage to deliver a therapeutically effective amount. Optimum dosage may vary depending on the efficacy of the individual ferrocenyl compounds.

The ferrocenyl compounds or pharmaceutically acceptable salts thereof, of the first aspect of the invention, or a pharmaceutical composition of the second aspect of the invention, may be used in combination with surgery, radiotherapy or other chemotherapy drugs.

According to a fifth aspect of the invention, there is provided the ferrocenyl compounds or pharmaceutically acceptable salts thereof, of the first aspect of the invention, or a pharmaceutical composition of the second aspect of the invention, for use in the treatment of a viral infection.

Such viral infections may include Herpes simplex virus 1 and 2, Vaccinia virus, Vesicular stomatitis virus, hepatitis C [HCV], HIV and Human cytomegalovirus [HCMV], influenza viruses and Human parainfluenza viruses.

Treatment may comprise administering a therapeutically effective amount of the ferrocenyl compounds or pharmaceutically acceptable salts thereof, of the first aspect of the invention, or a pharmaceutical composition of the second aspect of the invention, to a subject in need thereof.

It would be within the capability of the skilled person to work out an appropriate dosage to deliver a therapeutically effective amount. Optimum dosage may vary depending on the efficacy of the individual ferrocenyl compounds.

Figure 2:
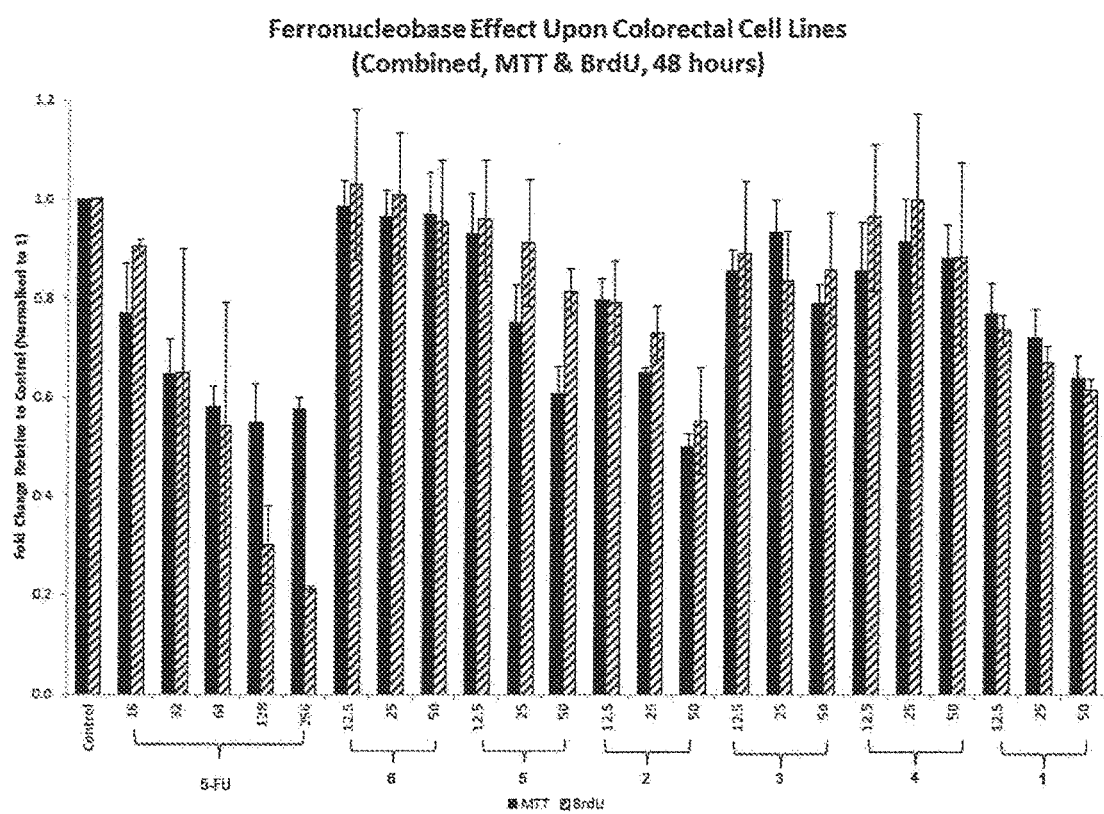

Embodiments of the invention will now be described by way of example only, with reference to the accompanying drawings in which:

FIG. 1 shows growth curves of ferrocenyl compounds 1 and 2, comparative compounds 3-5 and cisplatin in three different concentrations (LC=6.25 µM, MC=12.5 µM, HC=25 µM) over a 4-day experiment in cancer cell lines OE 19 and OE 33 respectively (n=3±SD), and FIG. 2 shows the effect of ferrocenyl compounds 1 and 2, comparative compounds 3-6 and fluorouracil (5-FU) on colorectal cell lines at various concentrations (µM).

Figure 3:
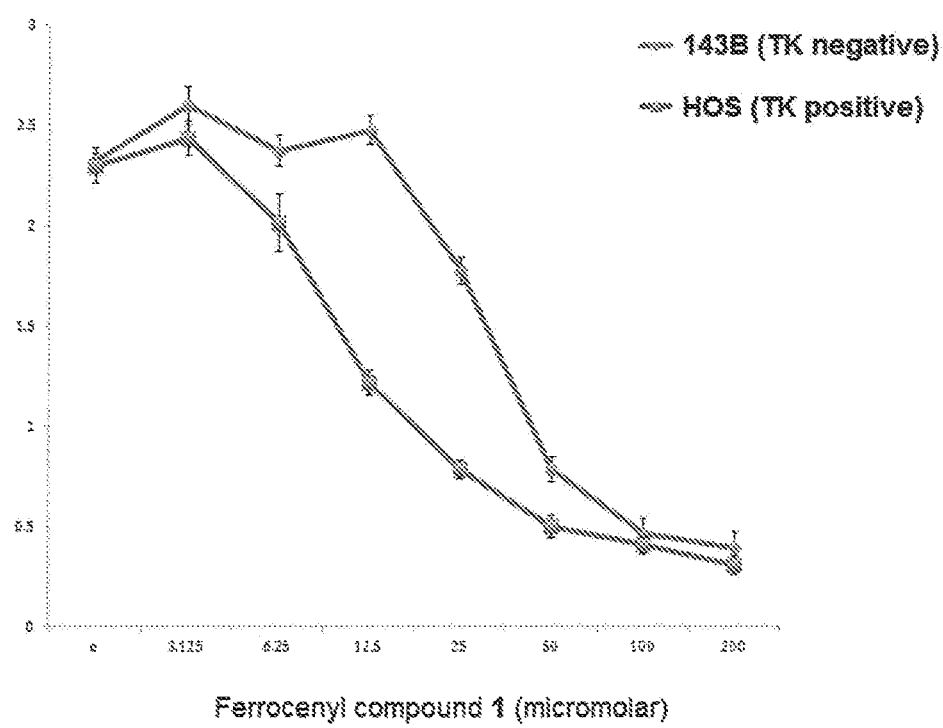

FIG. 3 shows cell death curves for ferrocenyl compound 1 in cells lacking the phosphorylation enzyme (TK negative) and in cells possessing the phosphorylation enzyme (TK positive).

SYNTHESES

Unless otherwise stated, solvents and reagents were obtained from commercial suppliers and used without further purification. Anhydrous solvents were obtained in-house from the solvent purification systems, SPS (Innovative Technology). Preparations of all target compounds were performed under argon. Column chromatography was carried out using silica gel (Merck, grade 60). $^1$H, $^{13}$C NMR spectra were recorded on Bruker AV 300 or AV 500. Electrospray mass spectra were measured by a Waters micromass LCT Electrospray Time-of-Flight (ES-TOF) mass spectrometer.

Synthesis of (S,R$_p$)-1-[α-Methyl-(3-(hydroxy)propyl)]-2-[(thyminyl)ethyl]-ferrocene (1) and (S,R$_p$)-1-[α-Methyl-(3-(hydroxy)propyl)]-2-[2-(-adenin-9-yl)ethyl]-ferrocene (2)

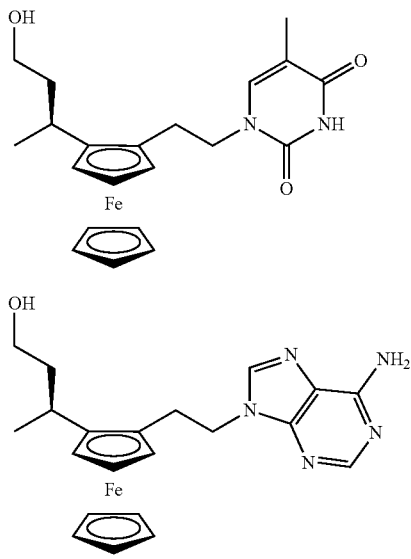

Ferrocenyl compounds 1 and 2, which fall within the scope of the claims, were synthesised as described below. It will be noted that ferrocenyl compound 1 comprises a pyrimidine nucleobase and a hydroxyl group. Ferrocenyl compound 2 comprises a purine nucleobase and a hydroxyl group.

The ferrocenyl compounds 1 and 2 have a disubstituted arrangement on one cyclopentadiene ring, with the other cyclopentadiene ring unfunctionalised and so exemplify compounds of the general formula (I) in which m is 1 and n is 0. Ferrocenyl compounds 1 and 2 have a 1,2-disubstituted arrangement of the heterocyclic moiety and hydroxyl substituents.

The synthetic route taken to make the ferrocenyl compounds 1 and 2 is shown in scheme 1 below. The chirally pure Ugi amine 7 was treated with n-BuLi and quenched with iodine to introduce the required the planar 1,2-disubstitution pattern. Subsequent functional group inter-conversion gave compound 11, to provide the chain extension to give a three carbon linker. Treatment of 11 with silyl enol ether, catalysized by the Lewis acid boron trifluoride, gave compound 12 in good yield. Reduction of the ester, followed by TBDPS protection gave compound 14. Conversion to carbonyl 15 (via n-BuLi halogen exchange and quenching with DMF) enabled a Wittig reaction to be performed, with subsequent hydroboration-oxidation of the product giving the mono-protected bis-alcohol 16 in high chiral purity (as checked by chiral HPLC analysis, 97% ee). The conversion of 16 to the ferrocenyl compounds 1 and 2 proceeded via a Mitsunobu reaction with the appropriate protected nucleobase, followed by deprotection of the protecting groups.

Scheme 1

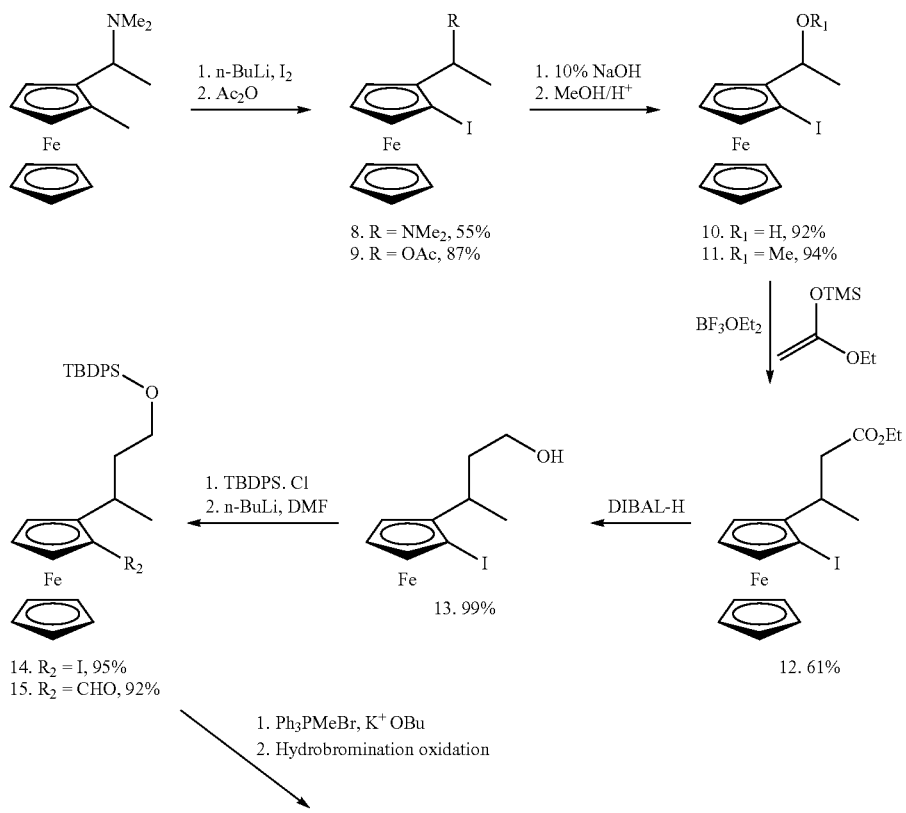

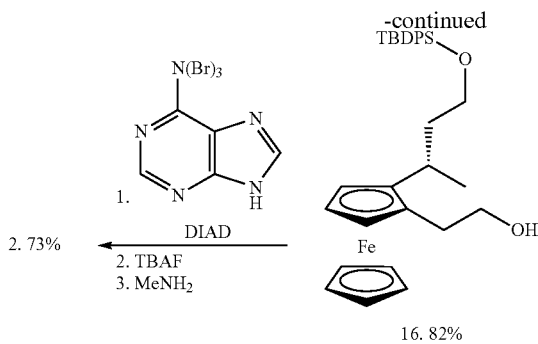
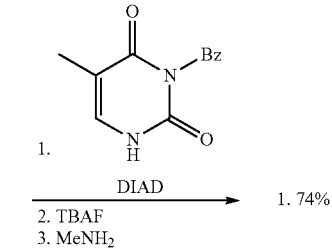

Preparation of (R,S$_p$)-1-(α-N,N-Dimethylamino-ethyl)-2-iodo-ferrocene (8)

For a preparation of Ugi amine 7 refer to Marquarding, D. et al., *J. Am. Chem. Soc.* 1970, 92, 5389.

In a 200 ml schlenk tube, Ugi amine 7 (4 g, 15 mmol) was dissolved in Et$_2$O (50 ml) at room temperature, n-BuLi (12 ml, 30 mmol) was added to the mixture at that temperature and stirred overnight under an inert atmosphere. The reaction mixture was cooled to −78° C. and Iodine (9.52 g, 37.5 mmol) dissolved in THF (60 ml) was added over the course of 10 min. The reaction was stirred at −78° C. for 90 min before allowing to warm to room temperature, at which point it was allowed to stirred for an additional 90 min before quenching at 0° C. with sodium thiosulfate$_{(aq)}$ (50 ml, 25% w/v). Dilute with Et$_2$O (30 ml), the layers were separated and the aqueous layer was further extracted with ether (50 ml×3). The combined organic fractions were dried over MgSO$_4$ solvent remove in vacuo and purified via flash column chromatography (5% MeOH, 5% TEA in DCM) to yield product (3.18 g, 55%). $^1$H NMR (400 MHz, CDCl$_3$) δ 4.46 (dd, J=2.4, 1.4 Hz, 1H), 4.24 (t, J=2.6 Hz, 1H), 4.15 (dd, J=2.7, 1.3 Hz, 1H), 4.12 (s, 5H), 3.62 (q, J=6.8 Hz, 1H), 2.15 (s, 6H), 1.50 (d, J=6.8 Hz, 3H). $^{13}$C NMR (101 MHz, CDCl$_3$) δ 90.21 (ipso Cp), 74.32 (Fc), 71.67 (Fc), 68.19 (Fc), 65.59 (Fc), 57.59 (CH*), 45.49 (ipso Cp), 41.22 (CH$_3$), 16.01 (CH$_3$). MS (ES) (m/z) calcd for C$_{14}$H$_{18}$N$^{56}$FeI 382.9833. found 382.9820. IR (cm$^{-1}$): 3078 (=C—H), 2931 (CH$_2$), 2878 (CH$_2$), 2809 (CH$_2$), 1446 (CH$_3$), 1371 (CH$_3$), 1243, 1087, 821 (CH=CH), 732 (CH Ar). Mp: melt at 58° C.-60° C. ⊐α⊐$_D$ (c=0.0022 g/ml, DCM)=+7.3.

Preparation of (R,S$_p$)-1-(α-Acetoxyethyl)-2-iodo-ferrocene (9)

In a 100 ml schlenk tube, 8 (3.26 g, 8.51 mmol) and acetic anhydride (25.68 ml, 272.17 mmol) were heated at 50° C. under inert atmosphere for 2 hrs. The excess acetic anhydrides were removed under high vacuum (0.1 mmHg). Purified via flash column chromatography (10% EtOAc in hexane) to yield the yellow-brown oily product (2.94 g, 87%). $^1$H NMR (400 MHz, CDCl$_3$) δ 5.89 (q, J=6.4 Hz, 1H), 4.51 (dd, J=2.6, 1.4 Hz, 1H), 4.33 (dd, J=2.8, 1.4 Hz, 1H), 4.28 (t, J=2.6 Hz, 1H), 4.15 (s, 5H), 2.01 (s, 3H), 1.66 (d, J=6.5 Hz, 3H). $^{13}$C NMR (101 MHz, CDCl$_3$) δ 170.30 (C=O), 87.54 (ipso Cp), 75.63 (Fc), 71.76 (Fc), 69.71 (Fc), 68.94 (Fc), 65.80 (CH*), 44.03 (ipso Cp), 21.16 (CH$_3$), 18.66 (CH$_3$). IR (cm$^{-1}$): 3095 (=C—H), 2972 (CH$_2$), 2928 (CH$_2$), 2866 (CH$_2$), 1729 (C=O), 1445 (CH$_3$), 1371 (CH$_3$), 1085, 820 (CH=CH), 703 (CH Ar). ⊐α⊐$_D$ (c=0.0086 g/ml, DCM)=−38.1.

Preparation of (R,S$_p$)-1-(α-Hydroxyethyl)-2-iodo-ferrocene (10)

In a 200 ml round bottom flask 9 (2.937 g, 7.37 mmol) was dissolved in EtOH (35 ml). NaOH$_{(aq)}$ (30 ml, 10% w/v) was added and the reaction was heated at 95° C. for 15 min. The reaction was allowed to cool to room temperature and organic layer was extracted with EtOAc (40 ml×2). The organic layers were dried over Na$_2$SO$_4$, solvent removed in vacuo and purified via flash column chromatography (25% EtOAc in hexane) to yield the yellow oily product (2.43 g, 92%) $^1$H NMR (400 MHz, CDCl$_3$) δ 4.85 (qd, J=6.5, 2.8 Hz, 1H), 4.46 (dd, J=2.5, 1.4 Hz, 1H), 4.29 (dd, J=2.7, 1.3 Hz, 1H), 4.25 (t, J=2.6 Hz, 1H), 4.14 (s, 5H), 1.88 (d, J=3.6 Hz, 1H), 1.62 (d, J=6.5 Hz, 3H). $^{13}$C NMR (101 MHz, CDCl$_3$) δ 91.61 (ipso Cp), 75.01 (Fc), 71.59 (Fc), 68.72 (Fc), 66.51 (Fc), 64.98 (CH*), 43.62 (ipso Cp), 21.31 (CH$_3$). MS (ES) (m/z) calcd for C$_{12}$H$_{13}$O$^{56}$FeI 355.9361. found 355.9352. IR (cm$^{-1}$): 3255 (OH), 3093 (=C—H), 2967 (CH$_2$), 2920 (CH$_2$), 1445 (CH$_3$), 1369 (CH$_3$), 1099 (C—OH), 816 (CH=CH), 684 (CH=CH). ⊐α⊐$_D$ (c=0.002 g/ml, DCM)=+12.0. Opposite enantiomer ⊐α⊐$_D$ (c=0.006 g/ml, DCM)=−24.7.

Preparation of (R,S$_p$)-1-(α-Methoxyethyl)-2-iodo-ferrocene (11)

In a 100 ml round bottom flask, 10 (2.43 g, 6.826 mmol) was dissolved in a MeOH/AcOH (20 ml, 9:1) mixture and the reaction was stirred at room temperature for 48 hrs. The reaction was quenched with water (10 ml) and extract with DCM (2×20 ml). The combined organic fractions were dried over MgSO$_4$, solvent removed in vacuo and purified via flash column chromatography (25% EtOAc in hexane) to yield the yellow oily product (2.37 g, 94%). $^1$H NMR (400 MHz, CDCl$_3$) δ 4.49 (dd, J=2.4, 1.4 Hz, 1H), 4.34 (q, J=6.5 Hz, 1H), 4.29-4.25 (m, 2H), 4.13 (s, 5H), 3.26 (s, 3H), 1.64 (d, J=6.5 Hz, 3H). $^{13}$C NMR (101 MHz, CDCl$_3$) δ 89.78 (ipso Cp), 74.78 (Fc), 74.22 (Fc), 71.66 (Fc), 68.86 (Fc), 65.35 (CH*), 56.00 (CH$_3$), 39.48 (ipso Cp), 19.63 (CH$_3$). MS (ES) (m/z) calcd for C$_{13}$H$_{15}$O$^{56}$FeI 369.9517. found 369.9513. IR (cm$^{-1}$): 3094 (=C—H), 2974 (CH$_2$), 2926 (CH$_2$), 2871 (CH$_2$), 2815 (CH$_2$), 1448 (CH$_3$), 1371 (CH$_3$), 1085 (C—O—C), 820 (CH=CH). ⊐α⊐$_D$ (c=0.0048 g/ml, DCM)=−16.7. Opposite enantiomer ⊐α⊐$_D$ (c=0.003 g/ml, DCM)=+33.3.

Preparation of (S,S$_p$)-1-[α-Methyl(2-ethylpropanoate)]-2-iodo-ferrocene (12)

In a 250 ml schlenk tube, 11 (2.37 g, 6.42 mmol) and 1-ethoxyvinyloxytrimethylsilane (8.234 g, 51.37 mmol)

were dissolved in DCM (30 ml). The mixture was cooled to −78° C. and BF$_3$.OEt$_2$ (1.774 ml, 14.12 mmol) was added drop wise. The reaction mixture was stirred for 15 min at −78° C. before allowing to be warmed to room temperature. Quenched with saturated NaHCO$_3$ (40 ml), the organic layer was separated and the aqueous layer was further extracted with DCM (40 ml). The combined organic fractions were dried over MgSO$_4$, solvent removed in vacuo and purified via flash column chromatography (10% EtOAc in hexane) to yield the yellow oily product (1.676 g, 61%). $^1$H NMR (400 MHz, CDCl$_3$) δ 4.42 (dd, J=2.4, 1.4 Hz, 1H), 4.18-4.08 (m, 8H+2H), 3.14-3.05 (m, 1H), 2.53 (dd, J=15.0, 3.7 Hz, 1H), 2.11 (dd, J=15.0, 10.3 Hz, 1H), 1.43 (d, J=6.9 Hz, 3H), 1.25 (t, J=7.2 Hz, 3H). $^{13}$C NMR (101 MHz, CDCl$_3$) δ 172.00 (C=O), 94.07 (ipso Cp), 74.12 (Fc), 71.52 (Fc), 67.84 (Fc), 64.58 (Fc), 60.26 (CH$_2$), 44.08 (ipso Cp), 43.19 (CH$_2$), 30.72 (CH*), 18.90 (CH$_3$), 14.27 (CH$_3$). MS (ES) (m/z) calcd for C$_{16}$H$_{19}$O$_2$$^{56}$FeI 425.9779. found 425.9782.

Preparation of (S,S$_p$)-1-[α-Methyl-(3-(hydroxyl)propyl)]-2-iodo-ferrocene (13)

In a 100 ml schlenk tube 12 (1.592 g, 3.73 mmol) was dissolved in Et$_2$O (50 ml), cooled to 0° C. and stand for 5 min. Diisobutylalumminum hydride (11.2 ml, 11.2 mmol) was added to the reaction slowly at that temperature. The reaction was allowed to stir at 0° C. for 1 hr before quenched with aqueous sodium potassium tartrate (30 ml). The layers were separated and the aqueous layer was further extract with Et$_2$O (30 ml). The combined organic fractions were dried over Na$_2$SO$_4$, solvent remove in vacuo and purified via flash column chromatography (50% EtOAc in hexane) to yield product (1.413 g, 99%). $^1$H NMR (400 MHz, CDCl$_3$) δ 4.42 (dd, J=2.4, 1.4 Hz, 1H), 4.17 (td, J=2.6, 0.6 Hz, 1H), 4.13 (s, 5H), 4.06 (dd, J=2.7, 1.3 Hz, 1H), 3.59 (t, J=6.6 Hz, 2H), 2.78-2.69 (m, 1H), 1.72-1.52 (m, 2H), 1.41 (d, J=7.0 Hz, 3H). $^{13}$C NMR (101 MHz, CDCl$_3$) δ 95.87 (ipso Cp), 73.76 (Fc), 71.47 (Fc), 67.87 (Fc), 64.18 (Fc), 60.84 (CH$_2$), 44.73 (ipso Cp), 42.09 (CH$_2$), 29.81 (CH*), 19.69 (CH$_3$). MS (ES) (m/z) calcd for C$_{14}$H$_{17}$O$^{56}$FeI 383.9674. found 383.9678. IR (cm$^{-1}$): 3282 br (OH), 3088 (=CH Fc), 2971 (CH$_2$), 2932 (CH$_2$), 2854 (CH$_2$), 1556, 1452 (CH$_2$), 1376 (CH$_3$), 680 (C=C). Mp: melt at 96° C.-98° C. ⊐α⊐$^D$ (c=0.0083 g/ml, DCM)=+16.9.

Preparation of (S,S$_p$)-1-[α-Methyl-(3-(tert-butyldiphenylsilyloxy)propyl)]-2-iodo-ferrocene (14)

In a 100 ml schlenk tube 13 (1.413 g, 3.67 mmol) was dissolved in 20 ml DCM at room temperature. TEA (0.769 ml, 5.52 mmol), tert-Butyldiphenylsilyl chloride (1.435 ml, 5.51 mmol) and DMAP in catalytic amount were added successively to the mixture. The solution was stirred overnight at room temperature and quenched with water. The phrases were separated and the aqueous layer was extracted with further Et$_2$O. The combined ethereal fractions were dried over Na$_2$SO$_4$, solvent removed in vacuo and purified via flash column chromatography (10% EtOAc in hexane) to yield a yellow oily product (2 g, 95%). $^1$H NMR (400 MHz, CDCl$_3$) δ 7.70-7.65 (m, 4H), 7.43-7.32 (m, 6H), 4.38 (dd, J=2.4, 1.3 Hz, 1H), 4.10 (s, 5H+1H), 4.00 (dd, J=2.7, 1.3 Hz, 1H), 3.70-3.65 (m, 2H), 2.77-2.68 (m, 1H), 1.88-1.80 (m, 1H), 1.43-1.34 (m, 1H), 1.31 (d, J=6.9 Hz, 3H), 1.05 (s, 9H). $^{13}$C NMR (101 MHz, CDCl$_3$) δ 135.63 (Ph), 134.10 (ipso Ph), 134.05 (ipso Ph), 129.47 (Ph), 127.58 (Ph), 96.25 (ipso Cp), 73.81 (Fc), 71.38 (Fc), 67.61 (Fc), 64.27 (Fc), 62.10 (CH$_2$), 44.45 (ipso Cp), 41.60 (CH$_2$), 30.03 (CH*), 26.94 (tBu), 19.24 (ipso tBu), 18.91 (CH$_3$). MS (ES) (m/z) calcd for C$_{30}$H$_{35}$O$^{56}$FeISiNa 622.0851. found 622.0846. IR (cm$^{-1}$): 3071 (=CH Fc), 2958 (CH$_2$), 2929 (CH$_2$), 2856 (CH$_2$), 1472 (CH$_2$), 1387 (CH$_3$), 1361, 1106, 1085, 821 (CH Ar TBDPS), 700 (C=C). ⊐α⊐$_D$ (c=0.008 g/ml, DCM)=−5.5.

Preparation of (S,S$_p$)-1-[α-Methyl-(3-(tert-butyldiphenylsilyloxy)propyl)]-2-aldehyde-ferrocene (15)

In a 100 ml schlenk tube 14 (2.182 g, 3.505 mmol) was dissolved in Et$_2$O (30 ml), the mixture was cooled to −78° C. and n-BuLi (2.32 ml, 7.011 mmol) was added. After 30 min, DMF (0.675 ml, 8.764 mmol) was added and the reaction was stirred at −78° C. for another 30 min before allowing too warm to room temperature, and then quenched with water (20 ml). The phases were separated and the aqueous layer was extracted with Et$_2$O (20 ml). The combined ethereal fractions were dried over Na$_2$SO$_4$, solvent removed in vacuo and purified via flash column chromatography (10% EtOAc in hexane) to yield the red oily product (1.686 g, 92%). $^1$H NMR (400 MHz, CDCl$_3$) δ 10.11 (s, 1H), 7.68-7.59 (m, 4H), 7.42-7.33 (m, 6H), 4.75 (dd, J=2.7, 1.4 Hz, 1H), 4.48 (t, J=2.6 Hz, 1H), 4.43 (dd, J=2.6, 1.4 Hz, 1H), 4.21 (s, 5H), 3.61 (t, J=7.1 Hz, 2H), 3.21-3.10 (m, 1H), 1.73-1.50 (m, 2H), 1.34 (d, J=6.9 Hz, 3H), 1.04 (s, 9H). $^{13}$C NMR (101 MHz, CDCl$_3$) δ 193.25 (C=O), 135.55 (Ph), 133.94 (ipso Ph), 133.80 (ipso Ph), 129.55 (Ph), 127.61 (Ph), 99.14 (ipso Cp), 76.31 (ipso Cp), 71.04 (Fc), 70.80 (Fc), 70.03 (Fc), 68.89 (Fc), 61.75 (CH$_2$), 43.28 (CH$_2$), 27.90 (CH*), 26.89 (tBu), 22.66 (ipso tBu), 19.17 (CH$_3$). MS (ES) (m/z) calcd for C$_{31}$H$_{36}$O$_2$$^{56}$FeSiNa 547.1732. found 547.1727. IR (cm$^{-1}$): 3071 (=CH Fc), 2958 (CH$_2$), 2929 (CH$_2$), 2856 (CH$_2$), 1673 (C=O), 1589 (C=N), 1427 (CH$_2$), 1376 (tBu), 1106 (Si—OR), 1086 (Si—OR), 821 (CH Ar Ph), 700 (C=C).

Preparation of (S,R$_p$)-1-[α-Methyl-(3-(tert-butyldiphenylsilyloxy)propyl)]-2-[2-(hydroxyl)ethyl]-ferrocene (16)

In a 100 ml schlenk tube, trimethylmethylphosphonium bromide (1.722 g, 4.821 mmol), potassium tert-butoxide (0.541 g, 4.821 mmol) and a catalytic amount of dibenzo-18-crown-6-ether were dissolved in 20 ml of dry THF. The mixture was stirred for 30 min and 15 (1.686 g, 3.214 mmol) was dissolved in 30 ml of dry THF and added to the mixture. The reaction was stirred overnight at room temperature, quenched with water and extracted with Et$_2$O (20 ml). The combined ethereal fractions were dried over Na$_2$SO$_4$, solvent removed in vacuo and purified via flash column chromatography (5% EtOAc in hexane) to yield the yellow oily product (1.497 g, 89%). $^1$H NMR (400 MHz, CDCl$_3$) δ 7.69-7.63 (m, 4H), 7.44-7.33 (m, 6H), 6.62 (dd, J=17.4, 10.8 Hz, 1H), 5.34 (dd, J=17.5, 1.8 Hz, 1H), 5.01 (dd, J=10.8, 1.7 Hz, 1H), 4.43 (dd, J=2.5, 1.4 Hz, 1H), 4.12 (t, J=2.6 Hz, 1H), 4.06 (dd, J=2.5, 1.4 Hz, 1H), 4.03 (s, 5H), 3.62 (dd, J=7.2, 5.4 Hz, 2H), 2.94-2.86 (m, 1H), 1.72-1.61 (m, 1H), 1.45-1.37 (m, 1H), 1.30 (d, J=6.8 Hz, 3H), 1.06 (s, 9H). $^{13}$C NMR (101 MHz, CDCl$_3$) δ 135.59 (Ph), 134.08 (ipso Ph), 134.02 (ipso Ph), 133.50 (CH vinyl), 129.49 (Ph), 127.56 (Ph), 110.96 (CH$_2$ vinyl), 94.84 (ipso Cp), 81.37 (ipso Cp), 69.66 (Fc), 66.55 (Fc), 66.27 (Fc), 64.08 (Fc), 61.89 (CH$_2$), 42.80 (CH$_2$), 27.65 (CH*), 26.89 (tBu), 19.23 (ipso tBu), 18.92 (CH$_3$). MS (ES) (m/z) calcd for C$_{32}$H$_{38}$O$^{56}$FeSi 522.2041. found 522.2055. IR (cm$^{-1}$): 3072 (=CH Fc), 2958 (CH$_2$) 2930 (CH$_2$), 2857 (CH$_2$), 1625 (Ar Ph), 1589, 1427 (CH$_2$), 1388 (CH$_3$), 1105 (Si—OR), 1086 (Si—OR), 821 (CH Ar), 699 (vinyl/C=C). In a 100 ml schlenk tube, the Wittig product (1.497 g, 2.865 mmol) was dissolved in 30 ml of dry THF. BH$_3$, THF (8.186 ml, 0.818 mmol) was then added drop wise at room temperature and stirred for 2 hrs. 9.762 ml of EtOH, 9.762 ml of NaOH (3M) and 7.174 ml of H$_2$O$_2$ (30%) were then successively added to the reaction and stirred for 1 hrs at room temperature. The reaction was extracted with DCM, washed with brine and dried over Na$_2$SO$_4$, solvent removed in vacuo and purified via flash column chromatography (10% EtOAc in hexane) to yield the yellow oily product (1.434 g, 82%). $^1$H NMR (400 MHz, CDCl$_3$) δ 7.68-7.64 (m, 4H), 7.43-7.36 (m, 6H), 4.11-4.09 (m, 1H), 4.05 (s, 5H), 4.00 (t, J=2.5 Hz, 1H), 3.97 (dd, J=2.5, 1.3 Hz, 1H), 3.75 (tq, J=6.8, 2.6 Hz, 2H), 3.67-3.63 (m, 2H), 2.77-2.68 (m, 1H), 2.66-2.49 (m, 2H), 1.74-1.66 (m, 1H), 1.43-1.32 (m, 1H), 1.26 (d, J=6.8 Hz, 3H), 1.06 (s, 9H). $^{13}$C NMR (101 MHz, CDCl$_3$) δ 135.56 (Ph), 133.96 (ipso Ph), 129.59 (Ph), 127.63 (Ph), 95.01 (ipso Cp), 82.31 (ipso Cp), 69.03 (Fc), 67.36 (Fc), 65.39 (Fc), 65.15 (Fc), 63.00 (CH$_2$), 61.98 (CH$_2$), 42.43 (CH$_2$), 30.93 (CH$_2$), 27.51 (CH*), 26.91 (tBu), 19.37 (CH$_3$), 19.22 (ipso tBu). MS (ES) (m/z) calcd for C$_{32}$H$_{40}$O$_2$$^{56}$FeSiNa 563.2045. found 563.2039. IR (cm$^{-1}$): 3378 br (OH), 3072 (=CH Fc), 2930 (CH$_2$), 2857 (CH$_2$), 1589, 1472 (CH$_3$), 1427 (CH$_2$), 1388 (tBu), 1361, 1105 (Si—OR), 1086 (Si—OR), 819 (CH Ar Ph), 705 (C=C). ⊐α⊐$_D$ (c=0.0056 g/ml, DCM)=−11.4. Opposite enantiomer ⊐α⊐$_D$ (c=0.0058 g/ml, DCM)=+23.5.

Preparation of (S,R$_p$)-1-[α-Methyl-(3-(hydroxy)propyl)]-2-[(thyminyl)ethyl]-ferrocene (1)

For a preparation of 3-benzoyl thymine refer to Cruickshank, A. K. et al., *Tetrahedron Lett.* 1984, 25, 681.

In a 100 ml schlenk tube, triphenylphosphine (137 mg, 0.516 mmol), 3-benzoyl thymine (95 mg, 0.447 mmol) and alcohol 16 (186 mg, 0.344 mmol) were dissolved in dry THF and stirred for 10 min at room temperature. The schlenk tube was then covered with foil and DIAD (0.11 ml, 0.516 mmol) was added at room temperature before the mixture was heated 65° C. for 2 hrs. The reaction was evaporated, extracted with EtOAc, washed with brine followed by water and dried over Na$_2$SO$_4$, solvent removed in vacuo and purified via flash column chromatography (30% EtOAc in hexane) to yield the fully protected product (219 mg, 85%). Deprotection was achieved by stirring the compound in 5 ml of TBAF for 2 hr, solvent was then removed. The mixture was redissolved in 2 ml of methylamine, stirred at room temperature for an addition 30 mins. The methylamine was evaporated. The crude was purified via flash column chromatography (5% MeOH in DCM) to yield product (105 mg, 74%). $^1$H NMR (400 MHz, CDCl$_3$) δ 9.44 (s, 1H), 7.07 (d, J=1.2 Hz, 1H), 4.16-4.02 (m, 8H), 3.99-3.88 (m, 1H), 3.74-3.55 (m, 3H), 2.96-2.47 (m, 4H), 1.95 (d, J=1.1 Hz, 3H), 1.75-1.64 (m, 1H), 1.56-1.46 (m, 1H), 1.39 (d, J=6.8 Hz, 3H). $^{13}$C NMR (101 MHz, CDCl$_3$) δ 164.22 (C=O), 151.11 (C=O), 140.41 (CH-thymine), 111.00 (ipso thymine), 95.36 (ipso Fc), 80.77 (ipso Fc), 69.30 (CH Cp), 67.63 (CH Cp), 65.97 (CH Cp), 65.37 (CH Cp), 60.27 (CH$_2$), 49.84 (CH$_2$), 43.24 (CH$_2$), 27.99 (CH$_2$), 27.07 (CH), 19.25 (CH$_3$ thymine), 12.30 (CH$_3$). MS (ES) (m/z) calcd for C$_{21}$H$_{26}$N$_2$O$_3$Na$^{56}$Fe 433.1191. found 433.1182.

Preparation of (S,R$_p$)-1-[α-Methyl-(3-(hydroxy)propyl)]-2-[2-(-adenin-9-yl)ethyl]-ferrocene (2)

In a 50 ml schlenk tube, triphenylphosphine (0.291 g, 1.109 mmol), N,N-6-dibenzoyl-adenine (0.381 g, 1.109 mmol) and alcohol 16 (0.300 g, 0.555 mmol) were dissolved in dry THF (10 ml) and stirred for 10 min at room temperature. The schlenk tube was then covered with foil and DIAD (0.244 ml, 1.109 mmol) was added at room temperature before the mixture was warmed up to 65° C. for 2 hrs. The reaction was evaporated, extracted with EtOAc, washed with brine followed by water and dried over Na$_2$SO$_4$, solvent removed in vacuo and purified via flash column chromatography (30% EtOAc in hexane) to yield fully protected product (0.343 g, 72%). $^1$H NMR (400 MHz, CDCl$_3$) δ 8.64 (s, 1H), 7.89-7.85 (m, 4H), 7.80 (s, 1H), 7.63-7.58 (m, 4H), 7.50-7.44 (m, 2H), 7.37-7.27 (m, 6H+4H), 4.38-4.21 (m, 2H), 4.06 (s, 5H), 3.98 (dd, J=2.4, 1.3 Hz, 1H), 3.96 (t, J=2.5 Hz, 1H), 3.69-3.63 (m, 2H+1H), 2.96-2.80 (m, 2H), 2.76-2.68 (m, 1H), 1.68-1.61 (m, 1H), 1.49-1.41 (m, 1H), 1.28 (d, J=6.7 Hz, 3H), 1.00 (s, 9H). $^{13}$C NMR (101 MHz, CDCl$_3$) δ 172.27 (C=O), 153.19 (ipso adenine), 152.15 (CH adenine), 151.63 (ipso adenine), 144.97 (CH adenine), 135.55 (Ph), 134.21 (ipso Bz), 133.75 (ipso adenine), 132.88 (Bz), 129.64 (Ph), 129.46 (Bz), 128.66 (Bz), 127.64 (Ph), 94.99 (ipso Cp), 80.88 (ipso Cp), 69.12 (Fc), 67.09 (Fc), 65.86 (Fc), 65.55 (Fc), 61.96 (CH$_2$), 44.71 (CH$_2$), 42.77 (CH$_2$), 28.52 (CH$_2$), 27.53 (CH*), 26.84 (tBu), 19.68 (CH$_3$), 19.16 (ipso tBu). Deprotection was achieved by stirring the compound in TBAF (5 ml, 1M) for 2 hr, solvent was then removed. The mixture was then redissolved in methylamine (2 ml, dissolved in ethanol), stirred at room temperature for an addition 30 mins. The methylamine was evaporated. Crude mixture was purified via flash column chromatography to obtain yellow solid was obtained (170 mg, 73%). $^1$H NMR (400 MHz, DMSO-d6) δ 8.19 (s, 1H), 8.17 (s, 1H), 7.21 (s, 2H), 4.41-4.33 (m, 2H+1H (OH)), 4.11 (s, 5H), 4.02 (d, J=2.4 Hz, 2H), 3.99 (t, J=2.4 Hz, 1H), 3.42-3.28 (m, 2H), 2.97-2.75 (m, 2H), 2.75-2.67 (m, 1H), 1.53-1.45 (m, 1H), 1.32 (d, J=6.8 Hz, 3H+1H). $^{13}$C NMR (101 MHz, DMSO-d6) δ 155.95 (ipso adenine), 152.43 (CH adenine), 149.39 (ipso adenine), 140.71 (CH adenine), 118.75 (ipso adenine), 94.43 (ipso Cp), 81.89 (ipso Cp), 68.80, 66.46, 64.92, 64.74, 58.66, 43.10, 42.43, 27.98, 27.10 (CH*), 19.38 (CH$_3$). MS (ES) (m/z) calcd for C$_{21}$H$_{26}$N$_5$O$^{56}$Fe 420.1487. found 420.1484. IR (cm$^{-1}$): 3348 br (OH), 3270 (NH$_2$), 3240 (NH$_2$), 3098 (=CH Fc), 2955 (CH$_2$), 2926 (CH$_2$), 2871 (CH$_2$), 1674 (C=N), 1604 (NH$_2$), 1574 (NH$_2$), 1305 (OH), 1076 (C—O), 814 (CH Ar). Mp: melt at 90° C.-92° C.

Synthesis of (S,R$_p$)-1-[α-methyl-(3-(hydroxy)propyl)]-2-[(thyminyl)propyl]-ferrocene (17)

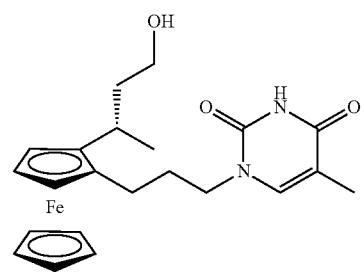

17

Ferrocenyl compound 17, which falls within the scope of the claims, was synthesised as described below (scheme 2). It will be noted that ferrocenyl compound 17 is analogous to ferrocenyl compound 1 except that the pyrimidine nucleobase is connected to the cyclopentadiene ring by a L1 linker which is n-propylene.

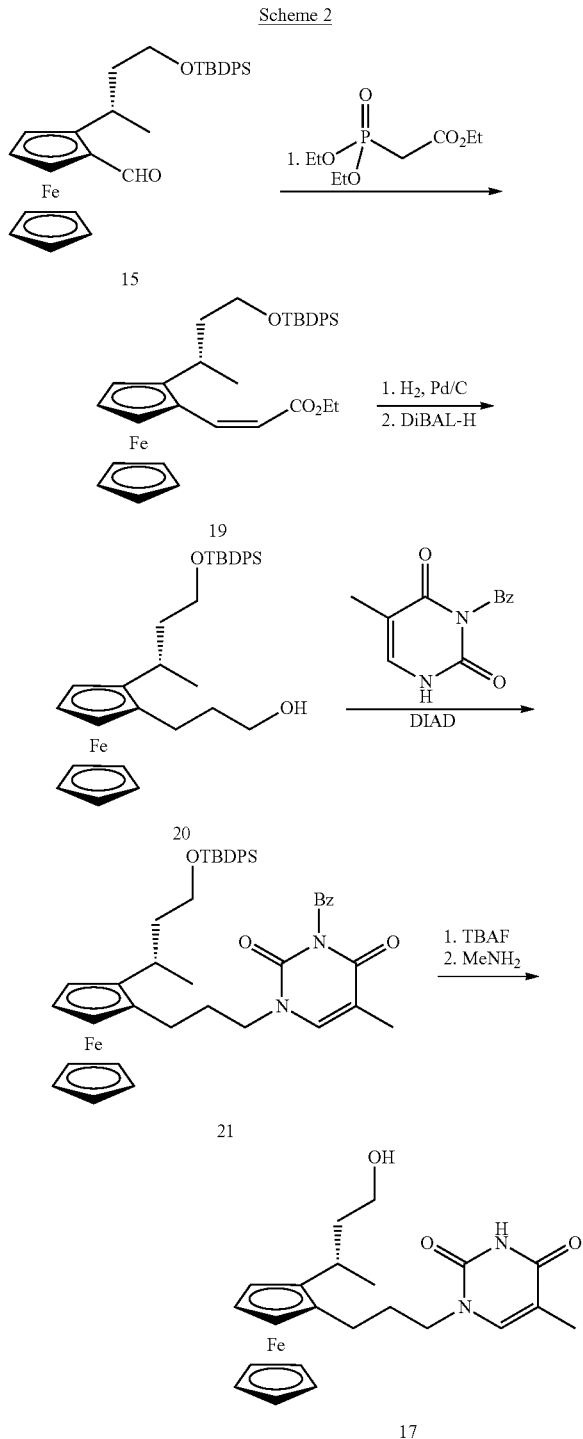

Scheme 2

The carbonyl intermediate 15, as obtained above, underwent a Horner-Wadsworth-Emmons reaction to extend the length of the alkylene L1 linker. Subsequent reduction of the double bond followed by ester reduction gave the monoprotected bis-alcohol 20. The conversion of 20 to the ferrocenyl compound 17 proceeded via a Mitsunobu reaction with the protected thymine nucleobase, followed by deprotection of the protecting groups.

Preparation of (S,$R_p$)-1-[α-Methyl-(3-(tert-butyldiphenylsilyloxy)propyl)]-2-[(2-Ethyloxycarbonyl)ethenyl]-ferrocene (19)

In a 200 ml schlenk tube triethyl phosphonoacetate (0.32 ml, 1.60 mmol) was dissolved in ethanol (10 ml). NaH (44 mg, 1.72 mmol, 95%) was added under an inert atmosphere. The mixture was allowed to stir at room temperature for 1 hr before 15 (600 mg, 1.14 mmol) dissolved in ethanol (10 ml) was added. After 16 hr the reaction mixture was quenched with water (100 ml), extract with EtOAc (40 ml×3). The combined organic fractions were dried over $MgSO_4$, solvent remove in vacuo and purified via flash column chromatography to yield product (518 mg, 76%). $^1$H NMR (300 MHz, $CDCl_3$) δ 7.49 (dd, J=10.3, 4.0 Hz, 4H), 7.37-7.15 (m, 6H), 5.89 (d, J=15.6 Hz, 1H), 4.57-3.79 (m, 11H), 3.45 (t, J=6.5 Hz, 2H), 2.83-2.56 (m, 1H), 1.65-1.30 (m, 2H), 1.14 (t, J=7.1 Hz, 6H), 0.92 (d, J=9.6 Hz, 9H).

Preparation of (S,$R_p$)-1-[α-Methyl-(3-(tert-butyldiphenylsilyloxy)propyl)]-2-[2-(hydroxyl)propyl]-ferrocene (20)

In a 100 ml round bottom flask with 19 (518 mg, 0.87 mmol) dissolved in EtOAc (10 ml) was added $Pd(OH)_2$ (20% wt. On carbon, 465 mg, 1.05 mmol). The reaction was stirred under $H_2$ (balloon pressure) atmosphere at room temperature for 16 hr, after which the mixture was filtered through a short pad of celite to yield a pale yellow solution. Solvent evaporated and the residue purified via flash column chromatography to yield product (500 mg, 96%). In a 100 ml schlenk tube, the product of 19 (500 mg, 0.84 mmol) was dissolved in diethyl ether (30 ml), cooled to 0° C. and stand for 5 mins. $LiAlH_4$ (38 mg, 1.00 mmol) was added to the reaction slowly at that temperature. The reaction was allowed to stir at 0° C. for 1 hr before quenched with aqueous sodium potassium tartrate (30 ml). The layers were separated and the aqueous layer was further extracted with diethyl ether (30 ml). The combined organic fractions were dried over $Na_2SO_4$, solvent remove in vacuo and purified via flash column chromatography to yield product (395 mg, 85%). $^1$H NMR (300 MHz, $CDCl_3$) δ 7.68 (ddd, J=7.8, 3.8, 1.8 Hz, 4H), 7.51-7.35 (m, 6H), 4.07 (s, 6H), 3.98 (s, 2H), 3.67 (dt, J=6.4, 3.9 Hz, 4H), 2.87-2.66 (m, 1H), 2.37 (ddd, J=21.2, 15.5, 7.6 Hz, 2H), 1.91-1.68 (m, 3H), 1.39 (ddd, J=14.8, 10.2, 5.2 Hz, 1H), 1.32-1.22 (m, 4H), 1.07 (s, 9H).

Preparation of (S,$R_p$)-1-[α-Methyl-(3-(tert-butyldiphenylsilyloxy)propyl)]-2-[(N3-benzoylthyminyl)propyl]-ferrocene (21)

In a 50 ml schlenk tube, triphenylphosphine (181 mg, 0.68 mmol) and the N-3-Benzoylthymine (116 mg, 0.54 mmol) were dissolved in dry THF and stirred for 10 min at room temperature. Compound 20 (250 mg, 0.45 mmol) was then added to the mixture pre-dissolved in 7 ml of dry THF. The schlenk tube was then covered with foil and DIAD (0.14 ml, 0.68 mmol) was added at room temperature before the mixture was warmed up to 65° C. for 1 hrs. The reaction was evaporated, dissolved with EtOAc, washed with brine followed by water and dried over $Na_2SO_4$, solvent removed in vacuo and purified via flash column chromatography (40% EtOAc in hexane) to yield product (235 mg, 68%). $^1$H NMR (300 MHz, CDCl$_3$) δ 7.95 (dd, J=8.4, 1.2 Hz, 2H), 7.76-7.58 (m, 5H), 7.58-7.33 (m, 8H), 6.87 (d, J=1.2 Hz, 1H), 4.09 (d, J=7.9 Hz, 6H), 4.02 (s, 2H), 3.80-3.51 (m, 4H), 2.83-2.70 (m, 1H), 2.48-2.30 (m, 2H), 1.95 (dd, J=15.2, 7.5 Hz, 2H), 1.89 (d, J=1.0 Hz, 3H), 1.73 (tdd, J=11.3, 7.5, 3.7 Hz, 1H), 1.50-1.37 (m, 1H), 1.28 (dd, J=6.8, 1.2 Hz, 3H), 1.10 (s, 9H).

Preparation of (S,R$_p$)-1-[α-methyl-(3-(hydroxy)propyl)]-2-[(thyminyl)propyl]-ferrocene (17)

Deprotection was achieved by stirring the compound 21 (100 mg, 0.13 mmol) in 5 ml of TBAF for 2 hr, solvent was then removed. The mixture was redissolved in 2 ml of methylamine, stirred at room temperature for an addition 30 mins. The methylamine was evaporated. The crude was purified via flash column chromatography (5% MeOH in DCM) to yield product (44 mg, 80%). $^1$H NMR (300 MHz, CDCl$_3$) δ 9.27 (s, 1H), 7.03 (s, 1H), 4.10-3.94 (m, 8H), 3.86-3.64 (m, 2H), 3.60 (t, J=6.3 Hz, 2H), 2.77 (m, 1H), 2.41 (dd, J=9.6, 6.7 Hz, 2H), 2.02-1.83 (m, 5H), 1.65-1.41 (m, 2H), 1.36 (d, J=6.9 Hz, 3H).

Synthesis of (S,R$_p$)-1-[α-methyl-(3-(hydroxy)propyl)]-2-[(thyminyl)methyl]-ferrocene (18)

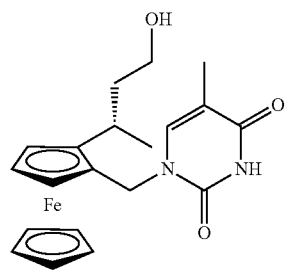

18

Ferrocenyl compound 18, which falls which the scope of the claims, was synthesised as described below (Scheme 3). It will be noted that ferrocenyl compound 18 is analogous to ferrocenyl compounds 1 and 17 except that the pyrimidine nucleobase is connected to the cyclopentadiene ring by a L1 linker which is methylene.

Scheme 3

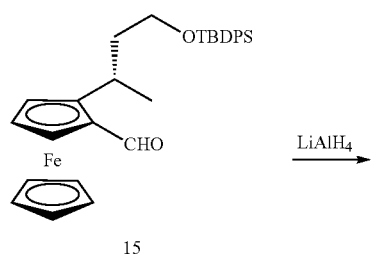

15

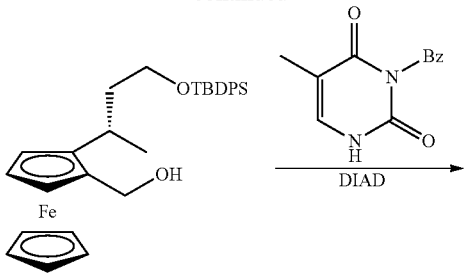

22

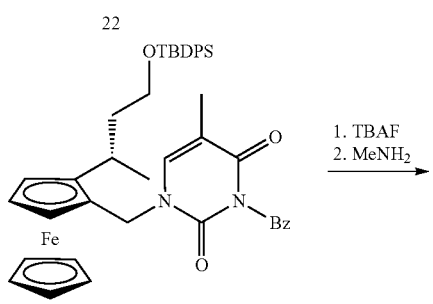

23

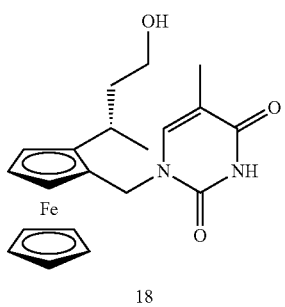

18

The carbonyl intermediate 15, obtained as above, underwent reduction to the mono-protected bis-alcohol 22. The conversion of 22 to the ferrocenyl compound 18 proceeded via a Mitsunobu reaction with the protected thymine nucleobase, followed by deprotection of the protecting groups.

Preparation of (S,R$_p$)-1-[α-Methyl-(3-(tert-butyldiphenylsilyloxy)propyl)]-2-[(hydroxyl)methyl]-ferrocene (22)

In a 100 ml schlenk tube, compound 15 (575 mg, 1.10 mmol) was dissolved in diethyl ether (20 ml), cooled to 0° C. and stand for 5 mins. LiAlH$_4$ (73 mg, 1.92 mmol) was added to the reaction slowly at that temperature. The reaction was allowed to stir at 0° C. for 1 hr before quenched with aqueous sodium potassium tartrate (30 ml). The layers were separated and the aqueous layer was further extracted with diethyl ether (30 ml). The combined organic fractions were dried over Na$_2$SO$_4$, solvent remove in vacuo and purified via flash column chromatography to yield product (473 mg, 82%). $^1$H NMR (300 MHz, CDCl$_3$) δ 7.67 (dd, J=20.7, 7.8, 1.7 Hz, 4H), 7.54-7.33 (m, 6H), 4.54 (dd, J=12.3, 5.0 Hz, 1H), 4.38-4.23 (m, 2H), 4.21-4.05 (m, 6H), 4.04-3.94 (m, 1H), 3.70-3.46 (m, 2H), 2.94 (dt, J=14.2, 7.1 Hz, 1H), 2.83 (dt, J=13.7, 6.9 Hz, 1H), 1.54-1.34 (m, 2H), 1.30 (d, J=6.9 Hz, 4H), 1.10 (s, 9H).

Preparation of (S,R$_p$)-1-[α-Methyl-(3-(tert-butyldiphenylsilyloxy)propyl)]-2-[(N3-benzoylthyminyl)methyl]-ferrocene (23)

In a 50 ml schlenk tube, triphenylphosphine (114 mg, 0.43 mmol) and the N-3-Benzoylthymine (73 mg, 0.34 mmol) were dissolved in dry THF and stirred for 10 min at room temperature. Compound 22 (150 mg, 0.28 mmol) was then added to the mixture pre-dissolved in 7 ml of dry THF. The schlenk tube was then covered with foil and DIAD (0.09 ml, 0.43 mmol) was added at room temperature before the mixture was warmed up to 65° C. for 1 hrs. The reaction was evaporated, dissolved with EtOAc, washed with brine followed by water and dried over Na$_2$SO$_4$, solvent removed in vacuo and purified via flash column chromatography (40% EtOAc in hexane) to yield product (151 mg, 72%). $^1$H NMR (300 MHz, CDCl$_3$) δ 7.84 (d, J=7.5 Hz, 2H), 7.55 (dt, J=11.3, 7.6 Hz, 5H), 7.34 (tt, J=13.5, 5.4 Hz, 8H), 7.09 (s, 1H), 4.62 (dd, J=50.5, 14.8 Hz, 2H), 4.33-3.88 (m, J=45.1 Hz, 8H), 3.78-3.46 (m, J=5.2 Hz, 2H), 2.75-2.54 (m, 1H), 1.78 (s, 3H), 1.69-1.55 (m, 1H), 1.39-1.27 (m, 1H), 1.13 (d, J=5.0 Hz, 3H), 0.99 (s, 9H).

Preparation of (S,R$_p$)-1-[α-methyl-(3-(hydroxy)propyl)]-2-[(thyminyl)methyl]-ferrocene (18)

Deprotection was achieved by stirring the compound 23 (151 mg, 0.204 mmol) in 5 ml of TBAF for 2 hr, solvent was then removed. The mixture was redissolved in 2 ml of methylamine, stirred at room temperature for an addition 30 mins. The methylamine was evaporated. The crude was purified via flash column chromatography (5% MeOH in DCM) to yield product (67 mg, 83%). $^1$H NMR (300 MHz, CDCl$_3$) δ 9.10 (s, 1H), 7.13 (s, 1H), 4.40-4.00 (m, 10H), 3.61 (t, J=6.4, 5.0 Hz, 2H), 2.97-2.84 (m, 1H), 1.88 (s, 3H), 1.55-1.08 (m, 5H).

It would be within the capability of the skilled person to determine methodology for accessing the other linker groups based on common general knowledge and known literature reactions. For instance, some of the synthetic routes outlined above, proceed via alkene intermediates (for example, alkene 19). Subsequent manipulation of such intermediates, but without reduction of the alkene double bond may allow access to alkenylene linker chains. Such alkene intermediates may also be converted into alkynylene linker chains. The synthetic routes outlined above proceed via alcohol intermediates (for example, alcohols 16, 20 and 22). Subsequent extension of these alcohols using the Williamson ether synthesis may provide access to alkyleneoxyalkylene linkers. Iodoferrocene intermediates may undergo Ullman-type couplings with alkoxides (as described in Schaarschmidt, D. et al., Organometallics 2010, 29, 4196) to provide alkyleneoxy linkers. Iodoferrocene intermediates may also be converted into hydroxyferrocene intermediates (as described in Onishi, M. et al., J. Organomet. Chem. 1984, 262, C11) for subsequent manipulation. Alkyleneamido linker chains may be accessible by hydrolysis of a suitable ferrocenyl ester intermediate to a carboxylic acid intermediate and reaction with an alcoholic amine. The synthesis of a ferrocenyl ester is described in Org. Lett. 2006, 8, 2763.

Synthesis of (24)

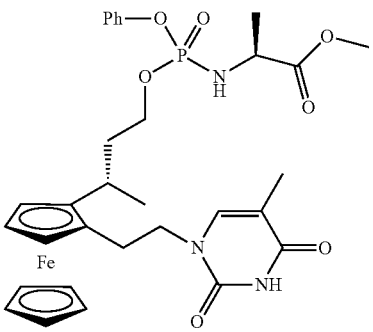

24

Ferrocenyl compound 24, which falls within the scope of the claims, was synthesised as described below (Scheme 4). Ferrocenyl compound 24 is analogous to ferrocenyl compound 1 except that the hydroxyl moiety has been converted into an aryloxyphosphoramidate.

Scheme 4

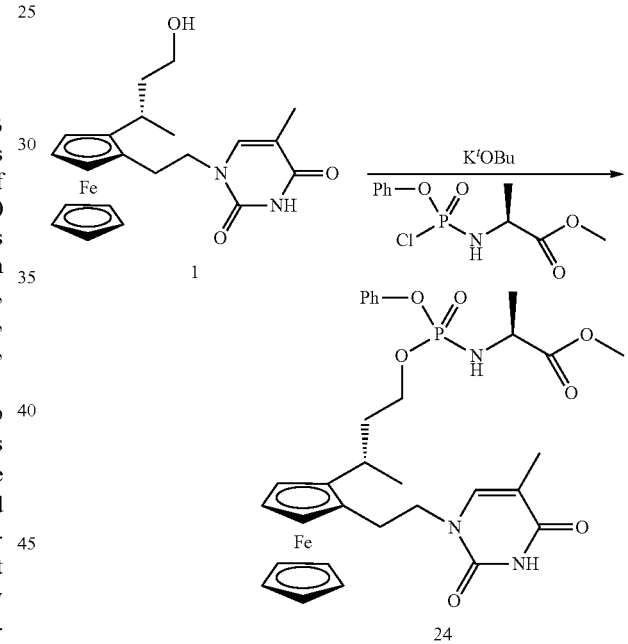

Preparation of (24)

For a preparation of phenyl-(methoxy-L-alaninyl)-phosphorochloridate refer to, for example, McGuigan, C. et al., J. Med. Chem. 1993, 36, 1048; McGuigan, C. et al., J. Med. Chem. 1996, 39, 1748; McGuigan, C. et al., Antiviral Res. 1997, 35, 195.

(S,R$_p$)-1-[α-Methyl-(3-(hydroxy)propyl)]-2-[(thyminyl)ethyl]-ferrocene (1) (100 mg, 0.2419 mmol) was dissolved in THF (10 ml), cooled to 00° C. and K$^t$OBu (14 mg, 0.1219 mmol) was added. After 20 mins, phenyl-(methoxy-L-alaninyl)-phosphorochloridate (34 mg, 0.1219 mmol) was added at this temperature and left to stir for 2 hrs. The reaction was quenched with water (5 ml) and extracted with DCM (20 ml), dried over MgSO$_4$ and purified by column chromatography. $^1$H NMR (400 MHz, CDCl$_3$) δ 9.26 (s, 1H), 7.33-7.25 (m, 3H), 7.23-7.17 (m, 2H), 7.12 (td, J=7.5, 1.0 Hz, 1H), 7.04 (s, 1H), 5.09 (t, J=10.2 Hz, 1H), 4.21-4.12 (m, 3H), 4.11-4.01 (m, 7H), 3.79 (s, 3H), 3.54-3.40 (m, 1H), 2.84-2.70 (m, 1H), 2.68-2.54 (m, 1H), 2.54-2.43 (m, 1H), 1.96 (s, 3H), 1.43 (d, J=7.1 Hz, 3H), 1.36 (d, J=6.8 Hz, 3H).

It would be within the capabilities of the skilled person to determine methodology for accessing other substituted phosphoramidates, substituted phosphates and substituted phosphonates from the hydroxyl moieties of the ferrocenyl compounds.

Syntheses of Comparative Compounds

The activity of ferrocenyl compounds 1 and 2 was compared with comparative compounds 3-6 to assess the role of the hydroxyl and heterocyclic groups.

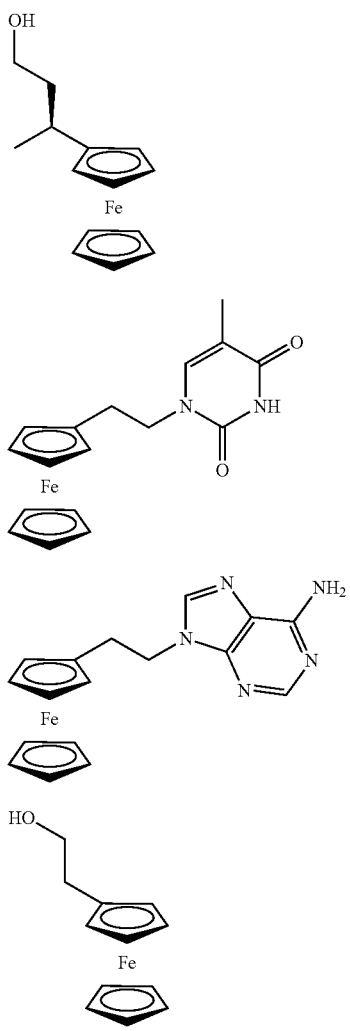

Comparative compounds 3-6 do not fall within the scope of the claims since they do not contain both a heterocyclic moiety and a hydroxyl group. It will be noted that comparative compounds 3 and 6 are each substituted with only a L2 linker to a hydroxyl group. Comparative compound 3 has the same L2 linker as ferrocenyl compounds 1 and 2. Comparative compound 6 has ethylene as the L2 linker. Comparative compound 6 has previously been shown to display antineoplastic activity against HeLa cells (Shago, F. R. et al., *Anticancer Res.* 2007, 27, 3431).

It will be noted that comparative compounds 4 and 5 are each substituted with only a L1 linker to a heterocyclic moiety which is a pyrimidine or purine nucleobase. Comparative compound 4 has the same L1 linker and heterocyclic moiety as in ferrocenyl compound 1, this being ethylene, which connects to a pyrimidine nucleobase. Comparative compound 5 has the same L1 linker and heterocyclic moiety as in ferrocenyl compound 2, this being ethylene, which connects to a purine nucleobase.

Comparative Compound 3

Synthesis of 1-[α-Methyl-(3-(hydroxy)propyl)]ferrocene (3)

For a preparation of (S)-3-Ethoxy-1-methyl-3-oxopropylferrocene refer to Locke, J. A. et al., *Organometallics* 1999, 18, 3750.

(S)-3-Ethoxy-1-methyl-3-oxopropylferrocene (220 mg, 0.733 mmol) was dissolved in diethyl ether (10 ml). LiAlH$_4$ (56 mg, 1.466 mmol) was added carefully, the resulting suspension was left to stir for 1 hr. Reaction was quenched with saturated sodium potassium tartrate (10 ml), extracted with diethyl ether (2×20 ml), dried over MgSO4, solvent removed in vacuo. Purified via flash column chromatography to give product as yellow oil (100 mg, 58%). $^1$H NMR (300 MHz, CDCl$_3$) δ 4.13 (s, 5H), 4.09-4.04 (m, 4H), 3.67 (q, J=6.2 Hz, 2H), 2.74-2.53 (m, 1H), 1.85-1.61 (m, 2H), 1.27 (d, J=6.9 Hz, 3H). $^{13}$C NMR (101 MHz, CDCl$_3$) δ 95.41 (ipso Cp), 68.51 (CH Cp), 67.22 (CH Cp), 67.12 (CH Cp), 67.07 (CH Cp), 65.70 (CH Cp), 61.12 (CH$_2$), 41.47 (CH$_2$), 29.62 (CH), 20.64 (CH$_3$). MS (ES) (m/z) calcd for C$_{14}$H$_{18}$O$_2$$^{56}$Fe 258.0707. found 258.0708.

Comparative Compound 4

Synthesis of 1-(Thyminyl-)ethyl-ferrocene (4)

For a preparation of N-3-benzoylthymine refer to Cruickshank, A. K. et al., *Tetrahedron. Lett.* 1984, 25, 681 and for a preparation of 2-ferrocenylethanol refer to Barry, P. K. et al., *Inorganica. Chimica. Acta.* 2009, 362, 2068.

In a 100 ml schlenk tube, triphenylphosphine (348 mg, 1.304 mmol), N-3-benzoylthymine (223 mg, 1.043 mmol), and 2-ferrocenylethanol (200 mg, 0.869 mmol) were dissolved in dry THF and stirred for 10 min at room temperature. The schlenk tube was then covered with foil and DIAD (0.28 ml, 1.304 mmol) was added at room temperature before the mixture was heated at 65° C. for 2 hrs. The reaction was evaporated, extracted with EtOAc, washed with brine followed by water and dried over Na$_2$SO$_4$, solvent removed in vacuo. The crude mixture was treated with methylamine solution (5 ml) for 30 min. The mixture was evaporated under vacuum and purified via flash column chromatography (40% EtOAc in hexane) to yield product (176 mg, 60%). $^1$H NMR (300 MHz, CDCl$_3$) δ 8.29 (s, 1H), 6.70 (d, J=1.2 Hz, 1H), 4.15 (s, 5H), 4.13-4.09 (m, 2H), 4.04 (t, J=1.8 Hz, 2H), 3.79 (t, J=7.1 Hz, 2H), 2.73 (t, J=7.1 Hz, 2H), 1.85 (d, J=1.2 Hz, 3H). MS (ES) (m/z) calcd for C$_{17}$H$_{18}$N$_2$O$_2$$^{56}$Fe 338.0718. found 338.0720. Mp: degraded at 235° C.

Comparative Compound 5

Synthesis of 1-[2-(Adenin-9-yl)ethyl]-ferrocene (5)

In a 50 ml schlenk tube triphenylphosphine (0.383 g, 1.46 mmol), N,N-6,6-dibenzoyl-adenine (0.500 g, 1.46 mmol) and 2-ferrocenylethanol (0.2 g, 0.729 mmol) were dissolved in dry THF (10 ml) and stirred for 10 min at room temperature. The schlenk tube was then covered with foil and DIAD (0.240 ml, 1.176 mmol) was added at room temperature before the mixture was warmed up to 65° C. for 2 hrs. The reaction was evaporated, extracted with EtOAc, washed with brine followed by water and dried over $Na_2SO_4$, solvent removed in vacuo and purified via flash column chromatography (40% EtOAc in hexane) to yield product (0.134 g, 33%). $^1$H NMR (400 MHz, $CDCl_3$) δ 8.69 (s, 1H), 7.86 (d, J=7.0 Hz, 4H), 7.76 (s, 1H), 7.48 (t, J=7.5 Hz, 2H), 7.34 (t, J=7.8 Hz, 4H), 4.34 (t, J=7.0 Hz, 2H), 4.11 (s, 5H), 4.06 (t, J=1.8 Hz, 2H), 3.86 (t, J=1.8 Hz, 2H), 2.90 (t, J=7.0 Hz, 2H). The bis-protected adenine ferrocenyl (0.055 g, 0.1 mmol) was dissolved in 3 ml of methylamine. The mixture was stirred at room temperature for half an hour under argon. The methylamine was then evaporated. The crude was purified on a silica gel chromatographic column with a 95/5 DCM/MeOH mix solvent. A yellow solid was obtained (0.019 g, 58%). $^1$H NMR (400 MHz, DMSO-d6) δ 8.17 (s, 1H), 8.05 (s, 1H), 7.17 (s, 2H), 4.31 (dd, J=8.2, 6.8 Hz, 2H), 4.15 (s, 5H), 4.08-4.02 (m, 4H), 2.85 (t, J=7.5 Hz, 2H). $^{13}$C NMR (101 MHz, DMSO-d6) δ 155.89 (ipso adenine), 152.35 (CH adenine), 149.40 (ipso adenine), 140.76 (CH adenine), 118.73 (ipso adenine), 84.39 (ipso Cp), 69.00 (Fc), 68.55 (Fc), 43.75 ($CH_2$), 29.34 ($CH_2$). MS (ES) (m/z) calcd for $C_{17}H_{18}N_5{}^{56}Fe$ 348.0912. found 348.0920 ($M^+ + H^+$). IR ($cm^{-1}$): 3399 ($NH_2$), 3316 ($NH_2$), 3084 (=CH Fc), 2980 ($CH_2$), 2931 ($CH_2$), 2907 ($CH_2$), 1653 (C=C), 1596 ($NH_2$), 1435 ($CH_2$), 1245, 797 (CH Ar). Mp: degrades at 142° C.

Cytotoxicity Studies

The cytotoxicity of ferrocenyl compound 1 and comparative compounds 3, 4 and 6 were tested in comparison to cisplatin using a proliferation activity assay carried out on three cell lines; murine leukemia cells (L1210), human cervix carcinoma cells (Hela) and non-cancerous human T-lymphocyte cells (CEM). The data indicate that the presence of both the hydroxyl and heterocyclic components give the highest $IC_{50}$ values, with ferrocenyl compound 1 exhibiting sub micromolar activity with an $IC_{50}$ value of 0.78 µM against L1210 cells compared with 1 µM for cisplatin (Table 1). In agreement with the literature on ferrocene alcohols (Shago, F. R. et al., Anticancer Res. 2007, 27, 3431), comparative compound 3 with a longer alkylene chain of three carbon atoms in length, gave higher $IC_{50}$ values than compound 6, with an ethylene chain. However, comparative compound 4 with only a heterocyclic moiety attached, gave poor cytotoxicity in these cell lines.

TABLE 1

Activity of ferrocenyl compounds (*50% inhibitory concentration)

| | $IC_{50}$* (µM) | | |
|---|---|---|---|
| Compound | L1210 | CEM | HeLa |
| 1 | 0.78 | 0.9 | 2.68 |
| 3 | 12.3 | 38.7 | 45.2 |
| 4 | 417 | 592 | 509 |
| 6 | 25 | 43 | 52 |
| Cisplatin | 1 | 0.9 | 1.2 |

Studies carried out on oesophageal cancer cell lines found that ferrocenyl compounds 1 and 2 inhibited cell growth at concentrations of 6.25 µM which is comparable to cisplatin as shown in FIG. 1. Once again the data indicated that both functional groups (the hydroxyl group in addition to the heterocyclic moiety, in these examples a nucleobase) were required to achieve the best activities; comparative compounds 3, 4 and 5 with only one of these components were ineffective at inhibiting cell growth, even at higher concentrations of 25 µM.

In further studies, assays of cellular viability (MTT assay) and cell proliferation (BrdU assay) were performed on colorectal cancer cell lines. MTT and BrdU assays are standard assays performed after the material is exposed to cell cultures. It would be within the capability of the skilled person to carry out these assays. The anticancer nucleobase analogue fluorouracil (5-FU) was used as a positive control, and the results after 48 hr exposure revealed that ferrocenyl compounds 1 and 2 had similar antineoplastic activity to that of 5-FU as shown in FIG. 2, whereas other compounds were less effective.

An AMES assay to test the potential mutagenicity of these ferrocenyl derivatives revealed a negative result.

Antiviral Studies

Ferrocenyl compound 1 was selected for testing against commercially available antiviral drugs as positive controls. The activity was comparable to known clinical drugs such as cidofovir (Table 2) against Herpes simplex virus 1 and 2 in Hela cells. Upon further testing with other cells such as Vero, CRFK and MDCK infected with viruses, it was found that ferrocenyl compound 1 was too toxic, with a low minimum cytotoxic concentration of <10 µM compared to commercially available drugs of between 100-250 µM.

TABLE 2

Antiviral activity assays of ferrocenyl compound 1 vs clinical drugs

| | | $EC_{50}{}^b$ (µM) | | | | |
|---|---|---|---|---|---|---|
| Compound | Minimum cytotoxic concentration$^a$ (µM) | Herpes simplex virus-1 (KOS) | Herpes simplex virus-2 (G) | Vaccinia virus | Vesicular stomatitis virus | Herpes simplex virus-1 TK$^-$ KOS ACV$^r$ |
| 1 (µM) | 244 | 2.4 | 2.4 | 21.6 | 48 | 9.6 |
| Brivudin (µM) | >250 | 0.02 | 183 | 10 | >250 | 50 |
| Cidofovir (µM) | >250 | 2 | 2 | 17 | >250 | 0.9 |
| Acyclovir (µM) | >250 | 0.4 | 0.4 | >250 | >250 | 50 |
| Ganciclovir (µM) | >100 | 0.03 | 0.03 | >100 | >100 | 10 |

$^a$Required to cause a microscopically detectable alteration of normal cell morphology.
$^b$Required to reduce virus-induced cytopathogenicity by 50%.

Phosphorylation Mechanism

The graph in FIG. 3 shows cell death curves for ferrocenyl compound 1 in cells lacking the phosphorylation enzyme (TK negative) and in cells possessing the phosphorylation enzyme (TK positive). It can be seen that the cells lacking the phosphorylation enzyme (TK negative) survive more than the cells that possess the phosphorylation enzyme (TK positive). This suggests that phosphorylation of the hydroxyl group is required for activation of ferrocenyl compound 1 and its subsequent incorporation into DNA to cause chain termination and cell death. Therefore, the use of masked phosphate groups, such as substituted phosphoramidates, for $R^1$ and/or $R^2$, which circumvent the need for the rate limiting first phosphorylation, may provide an increase in availability of the active compound and thus an improvement in efficacy in comparison with ferrocenyl compounds in which $R^1$ and/or $R^2$ is H.

CONCLUSIONS

Ferrocenyl compounds 1 and 2 appear to exhibit anticancer and/or antiviral activities that are comparable under the conditions used to commercially available drugs such as cisplatin and cidofovir. Control studies indicate that the presence of both a hydroxyl group and a heterocyclic moiety, such as a nucleobase, are required for optimal activity. This strongly suggests a mechanistic role for these novel organometallic compounds involving an adverse affect on nucleic acid synthesis, as is the case for nucleobase analogue drugs containing organic linker groups.

The invention claimed is:

1. A pharmaceutical composition comprising a ferrocenyl compound having the general formula (I);

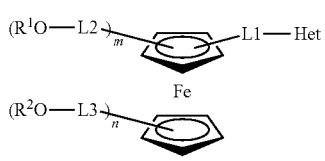
(I)

Wherein:
Het is a substituted or unsubstituted heterocyclic moiety;
L1, L2 and L3 are each a linker independently selected from alkylene, alkyleneoxy, alkyleneoxyalkylene, alkylenecarbonyl, alkyleneoxycarbonyl, alkyleneamido, alkyleneoxyamido, alkenylene, alkenyleneoxy, alkenylenecarbonyl, alkenyleneamido, alkynylene, alkynyleneoxy, alkynylenecarbonyl and alkynyleneamido, all of which may be straight chain or branched, substituted or unsubstituted;
$R^1$ and $R^2$ are each independently selected from H, substituted or unsubstituted alkylcarbonyl, substituted or unsubstituted arylcarbonyl, substituted or unsubstituted phosphate, substituted or unsubstituted phosphonate and substituted or unsubstituted phosphoramidate;
m and n are each 0 or 1; and
m+n≠0.

2. The pharmaceutical composition according to claim 1, wherein the linkers and ferrocenyl moiety are each independently represented by one of the formulae (II), (III) or (IV):

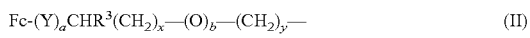 (II)

 (III)

 (IV)

wherein:
Fc is the ferrocenyl moiety;
Y is —(CO)—, —O— or (CO)NR$^4$;
$R^3$ is H, alkyl or halo;
$R^4$ is H or alkyl;
a and b are each 0 or 1;
x+y≤5; and
z≤4.

3. The pharmaceutical composition according to claim 2, wherein at least one of $R^3$ and $R^4$ is H.

4. The pharmaceutical composition according to claim 2, wherein at least one of a and b is 0.

5. The pharmaceutical composition according to claim 1, wherein the linker contains no more than 6 C atoms.

6. The pharmaceutical composition according to claim 1, wherein the substituted or unsubstituted heterocyclic moiety is a nitrogen containing heterocycle.

7. The pharmaceutical composition according to claim 1, wherein the substituted or unsubstituted heterocyclic moiety is aromatic.

8. The pharmaceutical composition according to claim 1, wherein the heterocyclic moiety is a substituted or unsubstituted pyrimidine or purine nucleobase.

9. The pharmaceutical composition according to claim 8, wherein the heterocyclic moiety is thymine or adenine.

10. The pharmaceutical composition according to claim 1, wherein m is 1 and n is 0.

11. The pharmaceutical composition according to claim 1, wherein m is 1, and L2-OR$^1$ and L1-Het are present in a 1,2-disubstituted arrangement on the cyclopentadiene ring.

12. The pharmaceutical composition according to claim 1, wherein at least one of $R^1$ and $R^2$ is

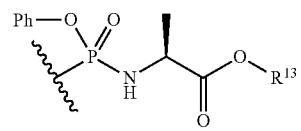

wherein $R^{13}$ is $C_1$ to $C_6$ alkyl, which may be linear or branched, substituted or unsubstituted or substituted or unsubstituted benzyl.

13. The pharmaceutical composition according to claim 1, wherein the ferrocenyl compound is in the form of a pharmaceutically acceptable salt thereof.

* * * * *